United States Patent
Richter et al.

[11] Patent Number: 5,990,084
[45] Date of Patent: Nov. 23, 1999

[54] COMPOUNDS WITH GROWTH HORMONE RELEASING PROPERTIES

[75] Inventors: Stefan Lutz Richter, Gentofte; Kjeld Madsen, Vaerlose; Henning Thogersen, Farum; Nils Langeland Johansen, Herlev; Ole Hvilsted Olsen, Bronshoj; Peter Hongaard Andersen, Vanlose; Annette Hansen, Vaerlose, all of Denmark

[73] Assignee: Novo Nordisk A/S, Bagsvaerd, Denmark

[21] Appl. No.: 08/844,031

[22] Filed: Apr. 18, 1997

Related U.S. Application Data

[60] Provisional application No. 60/021,869, Jul. 17, 1996.

[30] Foreign Application Priority Data

Apr. 19, 1996 [DK] Denmark .................................. 0468/96

[51] Int. Cl.$^6$ .............................. A61K 37/02; C07K 7/00
[52] U.S. Cl. .................................. 514/11; 514/9; 514/13; 514/14; 514/15; 530/317; 530/325; 530/326; 530/327; 530/328; 530/399
[58] Field of Search ...................................... 530/317, 325, 530/327–328, 399; 514/9, 11, 13, 14–15

[56] References Cited

FOREIGN PATENT DOCUMENTS

| 0 177 819 | 4/1986 | European Pat. Off. . |
| 8910933 | 11/1989 | WIPO . |
| WO/9218351 | 10/1992 | WIPO . |
| WO 94/11396 | 5/1994 | WIPO . |

*Primary Examiner*—Cecilia J. Tsang
*Attorney, Agent, or Firm*—Steve T. Zelson; Carol E. Rozek

[57] ABSTRACT

The present invention related to truncated GHRs of the general formula I $$K\text{-}(M)_x\text{-}A\text{-}B\text{-}(C)_w\text{-}D\text{-}E\text{-}(F)_z\text{-}G\text{-}(N)_y\text{-}L \qquad (I)$$

which have the ability to stimulate release of endogenous growth hormone.

77 Claims, No Drawings

COMPOUNDS WITH GROWTH HORMONE RELEASING PROPERTIES

CROSS REFERENCE TO RELATED APPLICATIONS

This application claim priority under 35 U.S.C. 119 of the U.S. provisional application Ser. No. 60/021,869 filed Jul. 17, 1996 and Danish application Serial no. 0468/96 filed Apr. 19, 1996, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration nonviable. Furthermore, other directly acting natural secretagogues, e.g., GHRH and PACAP, are longer polypeptides for which reason oral administration of them is not viable.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 95/17422, WO 95/17423 and WO 95/14666.

The composition of growth hormone releasing compounds is important for their growth hormone releasing potency as well as their bioavailability. It is therefore an object of the present invention to provide novel compounds with growth hormone releasing properties.

SUMMARY OF THE INVENTION

The present invention relates to compounds of the general formula I $$K-(M)_x-A-B-(C)_w-D-E-(F)_z-G-(N)_y-L \quad (I)$$

wherein

K, M, A, B, C, D, E, F, G, N, L, x, w, z and y are as defined below.

The compounds of formula I have the ability to stimulate synthesis and/or release of endogenous growth hormone. Thus, these compounds can be used in the treatment of conditions which require stimulation of growth hormone production or secretion such as in humans with growth hormone deficiency or were increased growth hormone plasma levels is desired like in the elderly or in animals used for food production.

DESCRIPTION OF THE INVENTION

The present invention relates to a compound of the general formula I $$K-(M)_x-A-B-(C)_w-D-E-(F)_z-G-(N)_y-L \quad (I)$$

wherein z and w are independently 0 or 1,

A and D are independently a non-proteinogenic or proteinogenic alpha amino acid residue of the general formula II

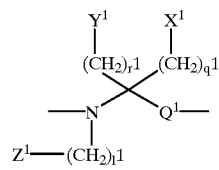

formula II wherein $Q^1$ is —$CH_2$— or —CO—, $l^1$, $q^1$ and $r^1$ are independently 0, 1, 2, 3, 4, 5, or 6, $X^1$ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, $Y^1$ is hydrogen, a $C_{1-6}$-alkyl group, or a valence bond to $X^1$ or $Z^1$ $Z^1$ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, B, C, E, F are independently a non-proteinogenic or proteinogenic alpha amino acid residue of the general formula III

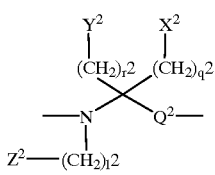

formula III wherein

Q² is —CH₂— or —CO—, l², q² and r² are independently 0, 1, 2, 3, 4, 5, or 6,

X² is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, Y² is hydrogen, a $C_{1-6}$-alkyl group, or a valence bond to X² or Z², Z² is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond;

or the residues of any of the following, non-proteinogenic amino acids (R- and S-isomer for chiral amino acids) dehydroalanine, anthranilic acid, 3-aminobenzoic acid, 4-aminobenzoic, 4-aminobutyric acid, beta-alanine, 3-amino-1,2,4-triazole-5-carboxylic acid, 1,2,3,4-tetrahyroisoquinoline-3-carboxylic acid, aminobiphenyl-carboxylic acids, pipecolic acid, nipecotinic acid, isonipecotinic acid, statine, 4-amino-3-hydroxybutyric acid, aminohexanoic acid, 2-amino-2-thiazoline4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans 2-aminocyclohexanecarboxylic acid, 4-aminomethylcyclohexanecarboxylic acid, 4-aminomethylbenzoic acid, aminonaphthoic aicd, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid;

G is a non-proteinogenic or proteinogenic alpha amino acid residue of the general formula IV

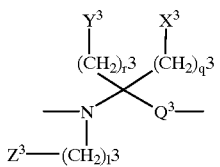

formula IV wherein

Q³ is —CH₂— or —CO—, l³, q³ and r³ are independently 0, 1, 2, 3, 4, 5, or 6,

X³ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, Y³ is hydrogen, a $C_{1-6}$-alkyl group, or a valence bond to X³ or Z³, Z³ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, M is an amino acid residue, a dipeptide residue, a tripeptide residue, a tetrapeptide residue, a pentapeptide residue, a hexapeptide residue, a heptapeptide residue, a octapeptide residue, a nonapeptide residue, a decapeptide residue, a undecapeptide residue, a dodecapeptide residue or a tredecapeptide residue, wherein the amino acid residues are independently any non-proteinogenic or proteinogenic alpha amino acid residue of the general formula V

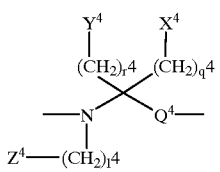

formula V wherein

Q⁴ is —CH₂— or —CO—, l⁴, q⁴ and r⁴ are independently 0, 1, 2, 3, 4, 5, or 6,

X⁴ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, Y⁴ is hydrogen, a $C_{1-6}$-alkyl group, or a valence bond to X⁴ or Z⁴, $Z^4$ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond;

or the residues of any of the following, non-proteinogenic amino acids (R- and S-isomer for chiral amino acids) dehydroalanine, anthranilic acid, 3-aminobenzoic acid, 4-aminobenzoic, 4-aminobutyric acid, beta-alanine, 3-amino-1,2,4-triazole-5-carboxylic acid, 1,2,3,4-tetrahyroisoquinoline-3-carboxylic acid, aminobiphenylcarboxylic acids, pipecolic acid, nipecotinic acid, isonipecotinic acid, statine, 4-amino-3-hydroxybutyric acid, aminohexanoic acid, 2-amino-2-thiazoline-4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans 2-aminocyclohexanecarboxylic acid, 4-aminomethylcyclohexanecarboxylic acid, 4-aminomethylbenzoic acid, aminonaphthoic acid, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid;

N is an amino acid residue, a dipeptide residue, an oligopeptide residue or an oligoamide residue which is between 1 to 10 amino acid residues long wherein the amino acid residues independently are any non-proteinogenic or proteinogenic alpha-amino acid residue of the general formula VI

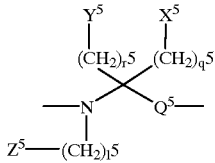

formula VI wherein $Q^5$ is —$CH_2$— or —CO—, $l^5$, $q^5$ and $r^5$ are independently 0, 1, 2, 3, 4, 5, or 6, $X^5$ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond, $Y^5$ is hydrogen, a $C_{1-6}$-alkyl group, or a valence bond to $X^5$ or $Z^5$, $Z^5$ is hydrogen, or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group, or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group, or a valence bond;

or the residues of any of the following, non-proteinogenic amino acids (R- and S-isomer for chiral amino acids) dehydroalanine, anthranilic acid, 3-aminobenzoic acid, 4-aminobenzoic, 4-aminobutyric acid, beta-alanine, 3-amino-1,2,4-triazole-5-carboxylic acid, 1,2,3,4-tetrahyroisoquinoline-3-carboxylic acid, aminobiphenylcarboxylic acids, pipecolic acid, nipecotinic acid, isonipecotinic acid, statine, 4-amino-3-hydroxybutyric acid, aminohexanoic acid, 2-amino-2-thiazoline-4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans 2-aminocyclohexanecarboxylic acid, 4-aminomethylcyclohexanecarboxylic acid, 4-aminomethylbenzoic acid, aminonaphthoic aicd, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid;

the total number of amino acid residues of N and M is equal to or less than 17;

x and y are independently 0 or 1;

when the sidechain of an amino acid residue of either M, A, B, C, D, E, F, G, or N contains an amino group, it can optionally be connected to a sidechain of an amino acid residue of M, A, B, C, D, E, F, G, or N containing a carboxylic acid group in order to generate a linkage of the general formula VII —[CO—$(CH_2)_{p}1$-(aryl)$_s$1-$(CH_2)_t1$-NH]$_{u}1$—  formula VII wherein $u^1$ and $s^1$ are independently 0, 1, or 2, $t^1$ and $p^1$ are independently 0, 1, 2, 3, 4, 5, 6, 7, or 8;

when a sidechain of an amino acid residue of either M, A, B, C, D, E, F, G, or N contains a mercapto group, it can optionally be connected to a side-chain of an amino acid residue of either M, A, B, C, D, E, F, G, or N containing an amino group in order to generate a linkage of the general formula VIII —$(CH_2)_{p}2$-(aryl)$_s$2-CO—  formula VIII wherein $p^2$ is 1, 2, 3, 4, or 5, $s^2$ is independently 0 or 1;

when a sidechain of an amino acid residue of either M, A, B, C, D, E, F, G, or N contains a mercapto group, it can optionally be connected to the methylene group of a dehydroalanine residue of either M, A, B, C, D, E, F, G, or N in order to generate a thioether linkage;

when the sidechains of two or more amino acid residues of M, A, B, C, D, E, F, G, or N contain a mercapto group, they can optionally be connected in order to generate a disulfide linkage;

K is $W^1$—$(CH_2)_{v}1$-CO—, or $W^2$—$(CH_2)_{v}2$-NH—CO—, or $W^3$—$(CH_2)_{v}3$-O—CO—, or $W^4$—$(CH_2)_{v}4$-$SO_2$—, wherein $v^1$, $v^2$, $v^3$ and $V^4$ independently are 0, 1, 2, 3, 4, 5, or 6, $W^1$, $W^2$, $W^3$ and $W^4$ independently are hydrogen, or a hydroxy, $C_{1-6}$-alkyl, aryl, amino group;

or a linkage to a sidechain of an amino acid residue of M, A, B, C, D, E, F, G, or N containing a carboxylic acid group of the general formula IX

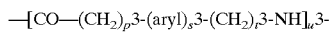 formula IX wherein $u^3$ and $s^3$ are independently 0, 1, or 2, $t^3$ and $p^3$ are independently 0, 1, 2, 3, 4, 5, 6, 7, or 8; or a linkage joining K and L of the general formula X

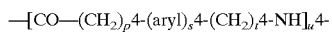 formula X wherein $u^4$ and $s^4$ are independently 0, 1, or 2, $t^4$ and $p^4$ are independently 0, 1, 2, 3, 4, 5, 6, 7, or 8;

L is —O—$(CH_2)_{p^5}$-$W^5$, wherein $p^5$ is 0, 1, 2, 3, 4, 5, or 6, $W^5$ is hydrogen, or a hydroxy, $C_{1-6}$-alkyl, aryl, amino group;

or L is

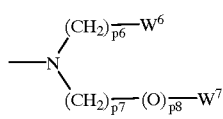

wherein $p^6$ and $p^7$ are independently 0, 1, 2, 3, 4, 5, or 6, $p^8$ is 0 or 1, $W^6$ and $W^7$ are independently hydrogen, or a hydroxy, $C_{1-6}$-alkyl, aryl, amino group, or a valence bond;

or a linkage to an amino group in the sidechain of an amino acid residue of M, A, B, C, D, E, F, G, or N of the general formula XI

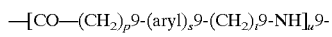 formula XI wherein $u^9$ and $s^9$ are independently 0, 1 or 2, $t^9$ and $p^9$ are independently 0, 1, 2, 3, 4, 5, 6, 7, or 8; or a pharmaceutically acceptable salt thereof.

In one embodiment of the compound of formula (I), A is a non-proteinogenic or proteinogenic amino acid of the general formula II

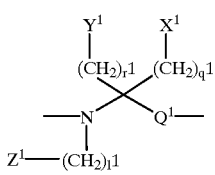

formula II wherein $Q^1$ is —$CH_2$— or —CO—, $l^1$ and $r^1$ are 0, $q^1$ is 0, 1, 2, 3, or 4, $X^1$ is hydrogen, isopropyl, tert. butyl, phenyl, cyclopropyl, cyclohexyl, 2-hydroxyethyl, or amino, $Y^1$ is hydrogen, or methyl, and $Z^1$ is hydrogen;

preferably A is the residue of leucine, isoleucine, valine, phenylalanine, cyclohexylalanine or homophenylalanine, more preferably leucine.

In another embodiment of the compound of formula (I), B is a non-proteinogenic or proteinogenic alpha amino acid residue of the general formula III

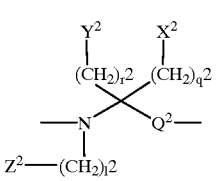

formula III wherein $Q^2$ is —$CH_2$— or —CO—, $l^2$ and $r^2$ are 0, $q^2$ is 0, 1, 2, 3, or 4, $X^2$ is hydrogen, phenyl, amino, guanidino, hydroxy, isopropyl, carboxy $Y^2$ is hydrogen, or methyl, $Z^2$ is hydrogen, or the residue of any of the following, non-proteinogenic amino acids; dehydroalanine, anthranilic acid, 3-aminobenzoic acid, 4-aminobenzoic, 4-aminobutyric acid, beta-alanine, cis- and trans 2-aminocyclohexanecarboxylic acid, 4-aminomethylcyclohexanecarboxylic acid or 4-aminomethylbenzoic acid;

preferably B is the residue of glycine, alanine, serine, lysine, ornithine, arginine, glutamic acid or aspartic acid, more preferably alanine.

In a further embodiment of the compound of formula (I), C is a non-proteinogenic or proteinogenic alpha amino acid residue of the general formula III

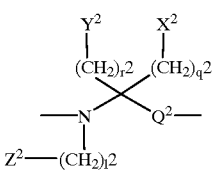

formula III wherein $Q^2$ is —$CH_2$— or —CO—, $l^2$ and $r^2$ are 0, $q^2$ is 0, 1, 2, 3, or 4, $X^2$ is hydrogen, imidazolyl, phenyl, amino, hydroxy, isopropyl, carboxy, aminocarbonyl, or guanidino, $Y^2$ is hydrogen or methyl, $Z^2$ is hydrogen;

preferably C is the residue of lysine, glutamine, glutamic acid, asparagine, aspartic acid, arginine, ornithine, serine or histidine, more preferably glutamine or ornithine.

In a further embodiment of the compound of formula (I), D is a non-proteinogenic or proteinogenic amino acid of the general formula II

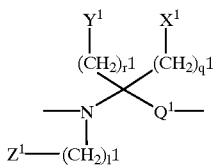

formula II wherein $Q^1$ is —$CH_2$— or —CO—, $l^1$ and $r^1$ are 0, $q^1$ is 0, 1, 2, 3, or 4, $X^1$ is hydrogen, isopropyl, tert. butyl, phenyl, cyclopropyl, cyclohexyl, 2-hydroxyethyl, or amino, $Y^1$ is hydrogen, or methyl, $Z^1$ is hydrogen;

preferably D is the residue of leucine, isoleucine, valine, phenylalanine, cyclohexylalanine or homophenylalanine, more preferably leucine.

In a further embodiment of the compound of formula (I), E is a non-proteinogenic or proteinogenic alpha amino acid residue of the general formula III

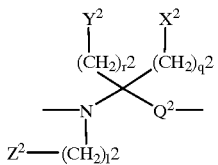

formula III wherein $Q^2$ is —$CH_2$— or —CO—, $l^2$ and $r^2$ are 0, $q^2$ is 0, 1, 2, 3, or 4, $X^2$ is hydrogen, phenyl, amino, guanidino, hydroxy, isopropyl, carboxy, $Y^2$ is hydrogen, or methyl, $Z^2$ is hydrogen, or the residue of any of the following, non-proteinogenic amino acids; dehydroalanine, anthranilic acid, 3-aminobenzoic acid, 4-aminobenzoic, 4-aminobutyric acid, beta-alanine, cis- and trans 2-aminocyclohexanecarboxylic acid, 4-aminomethylcyclohexanecarboxylic acid or 4-aminomethylbenzoic acid;

preferably E is the residue of glycine, alanine, serine, threonine, tyrosine, lysine, ornithine, glutamic acid, aspartic acid, homoarginine or arginine, more preferably serine.

In a further embodiment of the compound of formula (I), F is a non-proteinogenic or proteinogenic alpha amino acid residue of the general formula III

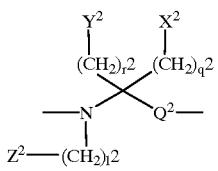

formula III wherein $Q^2$ is —$CH_2$— or —CO—, $l^2$ and $r^2$ are 0, $q^2$ is 0, 1, 2, 3, or 4, $X^2$ is hydrogen, phenyl, amino, hydroxy, isopropyl, carboxy, aminocarbonyl, or guanidino, $Y^2$ is hydrogen or methyl, $Z^2$ is hydrogen;

preferably F is the residue of alanine, phenylalanine, glycine, serine, valine, lysine, glutamine, glutamic acid, asparagine, aspartic acid or arginine, more preferably alanine.

In a further embodiment of the compound of formula (I), G is a non-proteinogenic or proteinogenic amino acid residue of the general formula IV

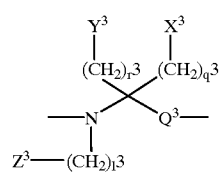

Formula IV wherein $Q^3$ is —$CH_2$— or —CO—, $l^3$ and $r^3$ are 0, $q^2$ is 0, 1, 2, 3, or 4, $X^2$ is amino, methylamino, dimethylamino, amidino, benzamidino, guanidino, imidazolyl, hydroxy, aminocarbonyl, $Y^2$ is hydrogen or methyl, $Z^2$ is hydrogen;

preferably G is the residue of arginine, lysine, glutamine, ornithine, histidine, serine or asparagine, more preferably arginine.

In a further embodiment of the compound of formula (I), M is the residue of valine, isoleucine, leucine, penicillamine, lysine, glutamic acid, glutamine, aspartic acid, arginine, alanine, cysteine, homocysteine, leucine, isoleucine, methionine, ornithine, phenylalanine or threonine, preferably valine.

In a further embodiment of the compound of formula (I), M is a dipeptide residue and the amino acid residue in the aminoterminal position of the dipeptide residue is the residue of lysine, arginine, ornithine, histidine, glutamine, alanine, glutamic acid, aspartic acid, asparagine, cysteine or serine, preferably lysine, aspartic acid or ornithine, the amino acid residue in the second position of the dipeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a tripeptide residue and the amino acid residue in the aminoterminal position of the tripeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the second position of the tripeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the third position of the dipeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a tetrapeptide residue and the amino acid residue in the aminoterminal position of the tetrapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the second position of the tetrapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the third position of the tetrapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the fourth position of the tetrapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a pentapeptide residue and the amino acid residue in the aminoterminal position of the pentapeptide residue is the residue of serine, alanine, cysteine, threonine, lysine, valine, asparagine, aspartic acid, glutamine or glutamic acid, preferably alanine, the amino acid residue in the second position of the pentapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the third position of the pentapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the fourth position of the pentapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the fifth position of the pentapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a hexapeptide residue and the amino acid residue in the aminoterminal position of the hexapeptide residue is the residue of asparagine, aspartic acid, glutamine, glutamic acid, serine, lysine, alanine, threonine, cysteine or ornithine, preferably aspartic acid, glutamine or ornithine, the amino acid residue in the second position of the hexapeptide residue is the residue of serine, alanine, cysteine, threonine, lysine, valine, asparagine, aspartic acid, glutamine or glutamic acid, preferably alanine, the amino acid residue in the third position of the hexapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the fourth position of the hexapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the fifth position of the hexapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the sixth position of the hexapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a heptapeptide residue and the amino acid residue in the aminoterminal position of the heptapeptide is the residue of threonine, serine, lysine, methionine, leucine, isoleucine, alanine, asparagine, glutamine, aspartic acid, glutamic acid, cysteine or histidine, preferably threonine, the amino acid residue in the second position of the heptapeptide residue is the residue of asparagine, aspartic acid, glutamine, glutamic acid, serine, lysine, alanine, threonine, cysteine or ornithine, preferably aspartic acid, glutamine or ornithine, the amino acid residue in the third position of the heptapeptide residue is the residue of serine, alanine, cysteine, threonine, lysine, valine, asparagine, aspartic acid, glutamine or glutamic acid, preferably alanine, the amino acid residue in the fourth position of the heptapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the fifth position of the heptapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the sixth position of the heptapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the seventh position of the heptapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is an octapeptide residue and the amino acid residue in the aminoterminal position of the octapeptide residue is the residue of phenylalanine, tyrosine, tryptophane, histidine, 1-naphthylalanine, 2-naphthylalanine, cyclohexylalanine or lysine, preferably phenylalanine, the amino acid residue in the second position of the octapeptide residue is the residue of threonine, serine, lysine, methionine, leucine, isoleucine, alanine, asparagine, glutamine, aspartic acid, glutamic acid, cysteine or histidine, preferably threonine, the amino acid residue in the third position of the octapeptide residue is the residue of asparagine, aspartic acid, glutamine, glutamic acid, serine, lysine, alanine, threonine, cysteine or ornithine, preferably aspartic acid, glutamine or ornithine, the amino acid residue in the fourth position of the octapeptide residue is the residue of serine, alanine, cysteine, threonine, lysine, valine, asparagine, aspartic acid, glutamine or glutamic acid, preferably alanine, the amino acid residue in the fifth position of the octapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the sixth position of the octapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the seventh position of the octapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the eighth position of the octapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a nonapeptide residue and the amino acid residue in the aminoterminal position of the nonapeptide residue is the residue of isoleucine, leucine, valine, alanine, threonine, phenylalanine or methionine, preferably isoleucine, the amino acid residue in the second position of the nonapeptide residue is the residue of phenylalanine, tyrosine, tryptophane, histidine, 1-naphthylalanine, 2-naphthylalanine, cyclohexylalanine or lysine, preferably phenylalanine, the amino acid residue in the third position of the nonapeptide residue is the residue of threonine, serine, lysine, methionine, leucine, isoleucine, alanine, asparagine, glutamine, aspartic acid, glutamic acid, cysteine or histidine, preferably threonine, the amino acid residue in the fourth position of the nonapeptide residue is the residue of asparagine, aspartic acid, glutamine, glutamic acid, serine, lysine, alanine, threonine, cysteine or ornithine, preferably aspartic acid, glutamine or ornithine, the amino acid residue in the fifth position of the nonapeptide residue is the residue of serine, alanine, cysteine, threonine, lysine, valine, asparagine, aspartic acid, glutamine or glutamic acid, preferably alanine, the amino acid residue in the sixth position of the nonapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the seventh position of the nonapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the eighth position of the nonapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the ninth position of the nonapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is a decapeptide residue and the amino acid residue in the aminoterminal position of the decapeptide residue is the residue of alanine, valine, serine, leucine, lysine, threonine, glycine, glutamine, asparagine or histidine, preferably alanine or asparagine, the amino acid residue in the second position of the decapeptide residue is the residue of isoleucine, leucine, valine, alanine, threonine, phenylalanine or methionine, preferably isoleucine, the amino acid residue in the third position of the decapeptide residue is the residue of phenylalanine, tyrosine, tryptophane, histidine, 1-naphthylalanine, 2-naphthylalanine, cyclohexylalanine or lysine, preferably phenylalanine, the amino acid residue in the fourth position of the decapeptide residue is the residue of threonine, serine, lysine, methionine, leucine, isoleucine, alanine, asparagine, glutamine, aspartic acid, glutamic acid, cysteine or histidine, preferably threonine, the amino acid residue in the fifth position of the decapeptide residue is the residue of asparagine, aspartic acid, glutamine, glutamic acid, serine, lysine, alanine, threonine, cysteine or ornithine, preferably aspartic acid, glutamine or ornithine, the amino acid residue in the sixth position of the decapeptide residue is the residue of serine, alanine, cysteine, threonine, lysine, valine, asparagine, aspartic acid, glutamine or glutamic acid, preferably alanine, the amino acid residue in the seventh position of the decapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the eighth position of the decapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the ninth position of the decapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the tenth position of the decapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is an undecapeptide residue and the amino acid residue in the aminoterminal position of the undecapeptide residue is the residue of asparagine, glutamine, serine, aspartic acid, glutamic acid, lysine, alanine, threonine, methionine, arginine, histidine or leucine, preferably aspartic acid, the amino acid residue in the second position of the undecapeptide residue is the residue of alanine, valine, serine, leucine, lysine, threonine, glycine, glutamine, asparagine or histidine, preferably alanine or asparagine, the amino acid residue in the third position of the undecapeptide residue is the residue of isoleucine, leucine, valine, alanine, threonine, phenylalanine or methionine, preferably isoleucine, the amino acid residue in the fourth position of the undecapeptide residue is the residue of phenylalanine, tyrosine, tryptophane, histidine, 1-naphthylalanine, 2-naphthylalanine, cyclohexylalanine or lysine, preferably phenylalanine, the amino acid residue in the fifth position of the undecapeptide residue is the residue of threonine, serine, lysine, methionine, leucine, isoleucine, alanine, asparagine, glutamine, aspartic acid, glutamic acid, cysteine or histidine, preferably threonine, the amino acid residue in the sixth position of the undecapeptide residue is the residue of asparagine, aspartic acid, glutamine, glutamic acid, serine, lysine, alanine, threonine, cysteine or ornithine, preferably aspartic acid, glutamine or ornithine, the amino acid residue in the seventh position of the undecapeptide residue is the residue of serine, alanine, cysteine, threonine, lysine, valine, asparagine, aspartic acid, glutamine or glutamic acid, preferably alanine, the amino acid residue in the eighth position of the undecapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the ninth position of the undecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the tenth position of the undecapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the eleventh position of the undecapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is an dodecapeptide residue and the amino acid residue in the aminoterminal position of the dodecapeptide residue is the residue of alanine, valine, leucine, serine, threonine, lysine, cysteine, glutamine, glutamic acid, asparagine, aspartic acid, glycine, N-methylalanine or histidine, preferably alanine or N-methylalanine, the amino acid residue in the second position of the dodecapeptide residue is the residue of asparagine, glutamine, serine, aspartic acid, glutamic acid, lysine, alanine, threonine, methionine, arginine, histidine or leucine, preferably aspartic acid, the amino acid residue in the third position of the dodecapeptide residue is the residue of alanine, valine, serine, leucine, lysine, threonine, glycine, glutamine, asparagine or histidine, preferably alanine or asparagine, the amino acid residue in the fourth position of the dodecapeptide residue is the residue of isoleucine, leucine, valine, alanine, threonine, phenylalanine or methionine, preferably isoleucine, the amino acid residue in the fifth position of the dodecapeptide residue is the residue of phenylalanine, tyrosine, tryptophan, histidine, 1-naphthylalanine, 2-naphthylalanine, cyclohexylalanine or lysine, preferably phenylalanine, the amino acid residue in the sixth position of the dodecapeptide residue is the residue of threonine, serine, lysine, methionine, leucine, isoleucine, alanine, asparagine, glutamine, aspartic acid, glutamic acid, cysteine or histidine, preferably threonine, the amino acid residue in the seventh position of the dodecapeptide residue is the residue of asparagine, aspartic acid, glutamine, glutamic acid, serine, lysine, alanine, threonine, cysteine or ornithine, preferably aspartic acid, glutamine or ornithine, the amino acid residue in the eighth position of the dodecapeptide residue is the residue of serine, alanine, cysteine, threonine, lysine, valine, asparagine, aspartic acid, glutamine or glutamic acid, preferably alanine, the amino acid residue in the ninth position of the dodecapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the tenth position of the dodecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the eleventh position of the dodecapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the twelvth position of the dodecapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), M is an tredecapeptide residue and the amino acid residue in the aminoterminal position of the tredecapeptide residue is the residue of tyrosine, histidine, phenylalanine, tryptophane, lysine, 1-naphthylalanine, 2-naphthylalanine, biphenylalanine, glutamine or asparagine, preferably tyrosine, the amino acid residue in the second position of the tredecapeptide residue is the residue of alanine, valine, leucine, serine, threonine, lysine, cysteine, glutamine, glutamic acid, asparagine, asparticacid, glycine, N-methylalanine or histidine, preferably alanine or N-methylalanine, the amino acid residue in the third position of the tredecapeptide residue is the residue of asparagine, glutamine, serine, aspartic acid, glutamic acid, lysine, alanine, threonine, methionine, arginine, histidine or leucine, preferably aspartic acid, the amino acid residue in the fourth position of the tredecapeptide residue is the residue of alanine, valine, serine, leucine, lysine, threonine, glycine, glutamine, asparagine or histidine, preferably alanine or asparagine, the amino acid residue in the fifth position of the tredecapeptide residue is the residue of isoleucine, leucine, valine, alanine, threonine, phenylalanine or methionine, preferably isoleucine, the amino acid residue in the sixth position of the tredecapeptide residue is the residue of phenylalanine, tyrosine, tryptophane, histidine, 1-naphthylalanine, 2-naphthylalanine, cyclohexylalanine or lysine, preferably phenylalanine, the amino acid residue in the seventh position of the tredecapeptide residue is the residue of threonine, serine, lysine, methionine, leucine, isoleucine, alanine, asparagine, glutamine, aspartic acid, glutamic acid, cysteine or histidine, preferably threonine, the amino acid residue in the eighth position of the tredecapeptide residue is the residue of asparagine, aspartic acid, glutamine, glutamic acid, serine, lysine, alanine, threonine, cysteine or ornithine, preferably aspartic acid, glutamine or ornithine, the amino acid residue in the ninth position of the tredecapeptide residue is the residue of serine, alanine, cysteine, threonine, lysine, valine, asparagine, aspartic acid, glutamine or glutamic acid, preferably alanine, the amino acid residue in the tenth position of the tredecapeptide residue is the residue of tyrosine, phenylalanine, histidine, glutamine, lysine, tryptophane, 1-naphthylalanine, 2-naphthylalanine, biphenylalanine, alanine, glutamic acid or cysteine, preferably tyrosine, the amino acid residue in the eleventh position of the tredecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, preferably arginine, the amino acid residue in the twelvth position of the tredecapeptide residue is the residue of lysine, arginine, ornithine, histidine, glutamine, alanine, glutamic acid, aspartic acid, asparagine, cysteine or serine, preferably lysine, ornithine or aspartic acid, the amino acid residue in the thirteenth position of the tredecapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine, preferably valine.

In a further embodiment of the compound of formula (I), N is the residue of lysine, histidine, ornithine, arginine, glutamine, glutamic acid, aspartic acid, asparagine, serine, alanine, cysteine, tyrosine, tryptophane, phenylalanine or homocysteine, preferably histidine or lysine.

In a further embodiment of the compound of formula (I), N is a dipeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the carboxyterminal position is the residue of leucine, alanine, cyclohexylalanine, glutamic acid, lysine, aspartic acid, cysteine, valine, isoleucine, methionine, histidine, threonine or phenylalanine, preferably leucine.

In a further embodiment of the compound of formula (I), N is a tripeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the carboxyterminal position is the residue of leucine, alanine, cyclohexylalanine, glutamic acid, lysine, aspartic acid, cysteine, valine, isoleucine, methionine, histidine, threonine or phenylalanine, preferably leucine.

In a further embodiment of the compound of formula (1), N is a tetrapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the carboxyterminal position is the residue of glutamine, glutamic acid, aspartic acid, asparagine, lysine, serine, arginine, ornithine, histidine, cysteine, methionine, threonine, tyrosine, alanine or leucine, preferably glutamine.

In a further embodiment of the compound of formula (I), N is a pentapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the carboxyterminal position is the residue of asparagine, histidine, glutamine, aspartic acid, glutamic acid, lysine, ornithine, serine, methionine, threonine or alanine, preferably histidine.

In a further embodiment of the compound of formula (I), N is a hexapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, preferably histidine, the amino acid residue in the carboxyterminal position is the residue of isoleucine, valine, threonine, glutamic acid, aspartic acid, lysine, cysteine, penicillamine, homocysteine, methionine, histidine, leucine or alanine.

In a further embodiment of the compound of formula (I), N is a heptapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably histidine or lysine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, preferably histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the carboxyterminal position is the residue of methionine, norleucine, homocysteine, leucine, glutamine, glutamic acid, aspartic acid, lysine, ornithine, histidine, threonine, asparagine, alanine or serine.

In a further embodiment of the compound of formula (I), N is an octapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably histidine or lysine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, preferably histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the carboxyterminal position is the residue of serine, threonine, alanine, cysteine, asparagine, aspartic acid, glutamic acid, glutamine, histidine, arginine, tyrosine or homocysteine.

In a further embodiment of the compound of formula (I), N is a nonapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably histidine or lysine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, preferably histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the carboxyterminal position is the residue of arginine, lysine, ornithine, histidine, glutamine, glutamic acid, asparagine, aspartic acid, serine, tyrosine, homocysteine or alanine.

In a further embodiment of the compound of formula (I), N is a decapeptide residue and the amino acid residue in the first position is the residue of lysine, histidine, ornithine, arginine, glutamine, glutamic acid, aspartic acid, asparagine, serine, alanine, cysteine, tyrosine, tryptophane, phenylalanine or homocysteine, preferably lysine or histidine, the amino acid residue in the second position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the third position is the residue of leucine, alanine, cyclohexylalanine, glutamic acid, lysine, aspartic acid, cysteine, valine, isoleucine, methionine, histidine, threonine or phenylalanine, preferably leucine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, preferably histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the ninth position is the residue of arginine, lysine, ornithine, histidine, glutamine, glutamic acid, asparagine, aspartic acid, serine, tyrosine, homocysteine or alanine, the amino acid residue in the carboxyterminal position is the residue of glutamine, glutamic acid, histidine, lysine, asparagine, aspartic acid, arginine, serine, threonine or tyrosine.

In a further embodiment of the compound of formula (I), K is hydrogen or a group of formula $W^1$—$(CH_2)_{v^1}$-CO—, wherein $W^1$ is hydrogen, hydroxy or $C_{1-6}$-alkyl, preferably hydrogen, and $v^1$ is 0, 1, 2, 3 or 4, preferably 1.

In a further embodiment of the compound of formula (I), L is

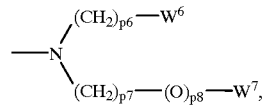

wherein $p^6$ and $p^7$ independently are 0, 1 or 2, preferably 0; $W^6$ is hydrogen, hydroxy or $C_{1-6}$-alkyl, preferably hydrogen; $p^8$ is 0 or 1, preferably 0; $W^7$ is hydrogen, hydroxy or $C_{1-6}$-alkyl, preferably hydrogen.

All of the above embodiments are independent of each other.

Preferred compounds of the invention are:
Asp-Ala-Tyr-Arg-Lys-Val-Leu-Ala-Gln-Leu-Ser-Ala-Arg-His-NH$_2$ (SEQ ID NO:1),
Ac-Asp-Ala-Tyr-Arg-Lys-Val-Leu-Ala-Gln-Leu-Ser-Ala-Arg-His-NH$_2$ (SEQ ID NO:2),
Asp-Ala-Tyr-Arg-Ala-Val-Leu-Ala-Gln-Leu-Ser-Ala-Arg-His-NH$_2$ (SEQ ID NO:3),
Asp-Tyr-Arg-Lys-Val-Leu-Ala-Gln-Leu-Ser-Ala-Arg-His-NH$_2$ (SEQ ID NO:4),
Asp-Ala-Tyr-Arg-Lys-Val-Leu-Ala-Gln-Leu-homoArg-His-NH$_2$ (SEQ ID NO:5),
Asp-Ala-Tyr-Arg-Ala-Val-Leu-Ala-Gln-Leu-homoArg-His-NH$_2$ (SEQ ID NO:6),
Asp-Tyr-Arg-Ala-Val-Leu-Ala-Gln-Leu-homoArg-His-NH$_2$ (SEQ ID NO:7),
Asp-Arg-Lys-Val-Leu-Ala-Gln-Leu-Ser-Ala-Arg-His-NH$_2$ (SEQ ID NO:8),
Asp-Lys-Val-Leu-Ala-Gln-Leu-Ser-Ala-Arg-His-NH$_2$ (SEQ ID NO:9),
Asp-Val-Leu-Ala-Gln-Leu-Ser-Ala-Arg-His-NH$_2$ (SEQ ID NO:10),
Asp-Leu-Ala-Gln-Leu-Ser-Ala-Arg-His-NH$_2$ (SEQ ID NO:11),
Ac-Asp-Ala-Tyr-Arg-Lys-Val-Leu-Ala-Glu-Leu-Ser-Ala-Arg-His-NH$_2$ (SEQ ID NO:12),
Asp-Ala-Tyr-Arg-Lys-Val-Leu-Ala-Glu-Leu-Ser-Ala-Arg-His-NH$_2$ (SEQ ID NO:13), Cyclo(Glu$^9$-Lys$^{13}$)-Asp-Ala-Tyr-Arg-Lys-Val-Leu-Ala-Glu-Leu-Ser-Ala-Lys-His-NH$_2$ (SEQ ID NO:14),
Cyclo(Lys$^5$-Glu$^9$)-Asp-Ala-Tyr-Arg-Lys-Val-Leu-Ala-Glu-Leu-Ser-Ala-Arg-His-NH$_2$ (SEQ ID NO:15),
Asp-Tyr-Arg-Lys-Val-Leu-Glu-Gln-Leu-Arg-His-NH$_2$ (SEQ ID NO:16),
Asp-Ala-Tyr-Arg-Lys-Val-Phe-Ala-Gln-Leu-Ser-Ala-Arg-His-NH$_2$ (SEQ ID NO:17),
Asp-Ala-Tyr-Arg-Lys-Val-Leu-Ala-Gln-Phe-Ser-Ala-Arg-His-NH$_2$ (SEQ ID NO:18),
Asp-Ala-Tyr-Arg-Lys-Val-Leu-Ala-Gln-Leu-Tyr-Ala-Arg-His-NH$_2$ (SEQ ID NO:19),
Asp-Ala-Gln-Arg-Lys-Val-Leu-Ala-Gln-Leu-Ser-Ala-Arg-His-NH$_2$ (SEQ ID NO:20),
Glu-Val-Leu-Arg-Glu-Leu-Ser-Ala-Arg-His-NH$_2$ (SEQ ID NO:21),
Cyclo(Asp$^1$-[Gly]-Orn$^5$)-Asp-Ala-Tyr-Arg-Orn-Val-Leu-Ala-Gln-Leu-Ser-Ala-Arg-His-NH$_2$ (SEQ ID NO:22),
Lys-Val-Leu-Ala-Gln-Leu-Ser-Ala-Arg-Lys-Leu-Leu-Gln-His-NH$_2$ (SEQ ID NO:23),
Asp-Ala-Tyr-Arg-Lys-Val-Leu-Ala-Gln-Leu-Ser-Ala-Lys-His-NH$_2$ (SEQ ID NO:24),
Ac-Asp-Ala-Tyr-Arg-Lys-Val-Leu-Ala-Gln-Leu-Ser-Ala-Lys-His-NH$_2$ (SEQ ID NO:25),
Cyclo(Lys$^2$-Glu$^6$)-Arg-Lys-Val-Leu-Ala-Glu-Leu-Ser-Ala-Arg-His-NH$_2$ (SEQ ID NO:26),
Cyclo(Lys$^4$-Glu$^8$)-Lys-Val-Leu-Lys-Gln-Leu-Ser-Glu-Arg-NH$_2$ (SEQ ID NO:27),
Cyclo(Orn$^2$-[COCH$_2$]-Pen$^6$)-(Asp-Orn-Tyr-Arg-Lys-Pen-Leu-Ala-Gln-Leu-Ser-Ala-Arg-His-NH$_2$ (SEQ ID NO:28),
Lys-Val-Leu-Ala-Gln-Leu-Ser-Ala-Arg-NH$_2$ (SEQ ID NO:29),
Cyclo(Lys$^3$-Glu$^7$)-Lys-Val-Leu-Lys-Gln-Leu-Ser-Glu-Arg-His-NH$_2$ (SEQ ID NO:30)
Cyclo(Lys$^2$-Glu$^6$)-Arg-Lys-Val-Leu-Ala-Glu-Leu-Ser-Ala-Arg-His-NH$_2$ (SEQ ID NO:31)
Cyclo(Lys$^3$-Glu$^7$)-Tyr-Arg-Lys-Val-Leu-Ala-Glu-Leu-Ser-Ala-Arg-His-NH$_2$ (SEQ ID NO:32)
Cyclo(Glu$^1$-Lys$^5$)-Glu-Ala-Tyr-Arg-Lys-Val-Leu-Ala-Glu-Leu-Ser-Ala-Arg-His-NH$_2$ (SEQ ID NO:33)
Cyclo(Lys$^4$-Glu$^8$)-Asp-Ala-Tyr-Lys-Lys-Val-Leu-Glu-Gln-Leu-Ser-Ala-Arg-His-NH$_2$ (SEQ ID NO:34)
Cyclo(Lys$^3$-Glu$^7$)-Ala-Tyr-Lys-Lys-Val-Leu-Glu-Gln-Leu-Ser-Ala-Arg-His-NH$_2$ (SEQ ID NO:35)
Cyclo(Lys$^4$-Glu$^8$)-Ala-Tyr-Arg-Lys-Val-Leu-Ala-Glu-Leu-Ser-Ala-Arg-His-NH$_2$ (SEQ ID NO:36),
Arg-Lys-Val-Leu-Ala-Gln-Leu-Ser-Ala-Arg-NH$_2$ (SEQ ID NO:37),
H-Tyr-Ala-Asp-Ala-Ile-Phe-Thr-Asp-Ala-Tyr-Arg-Lys-Val-Leu-Ala-Gln-Leu-Ser-Ala-Arg-His-NH$_2$ (SEQ ID NO:38),
Ac-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:39),
Ac-Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:40),
Cyclo(Asp$^2$-[gly]-Orn$^6$)-Ac-Asp-Asp-Ile-Phe-Thr-Orn-Ala-Tyr-Arg-Lys-Val-Leu-Ala-Gln-Leu-Ser-Ala-Arg-Lys-Leu-Leu-Gln-His-NH$_2$ (SEQ ID NO:41),
Cyclo(Asp$^6$-[gly]-Orn$^{10}$)-Ac-Asp-Ala-Ile-Phe-Thr-Asp-Ala-Tyr-Arg-Orn-Val-Leu-Ala-Gln-Leu-Ser-Ala-Arg-Lys-Leu-Leu-Gln-His-NH$_2$ (SEQ ID NO:42),
Cyclo(Asp$^{10}$-[gly]-Orn$^{14}$)-Ac-Asp-Ala-Ile-Phe-Thr-Asp-Ala-Tyr-Arg-Asp-Val-Leu-Ala-Orn-Leu-Ser-Ala-Arg-Lys-Leu-Leu-Gln-His-NH$_2$ (SEQ ID NO:43), or
Ac-(N-Me)Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:44).

Particular preferred compounds of the invention are:
H-Tyr-Ala-Asp-Ala-Ile-Phe-Thr-Asp-Ala-Tyr-Arg-Lys-Val-Leu-Ala-Gln-Leu-Ser-Ala-Arg-His-NH$_2$ (SEQ ID NO:38),
Ac-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:39),
Ac-Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:40),
Cyclo(Asp$^2$-[gly]-Orn$^6$)-Ac-Asp-Asp-Ile-Phe-Thr-Orn-Ala-Tyr-Arg-Lys-Val-Leu-Ala-Gln-Leu-Ser-Ala-Arg-Lys-Leu-Leu-Gln-His-NH$_2$ (SEQ ID NO:41),
Cyclo(Asp$^6$-[gly]-Orn$^{10}$)-Ac-Asp-Ala-Ile-Phe-Thr-Asp-Ala-Tyr-Arg-Orn-Val-Leu-Ala-Gln-Leu-Ser-Ala-Arg-Lys-Leu-Leu-Gln-His-NH$_2$ (SEQ ID NO:42),
Cyclo(Asp$^{10}$-[gly]-Orn$^{14}$)-Ac-Asp-Ala-Ile-Phe-Thr-Asp-Ala-Tyr-Arg-Asp-Val-Leu-Ala-Orn-Leu-Ser-Ala-Arg-Lys-Leu-Leu-Gln-His-NH$_2$ (SEQ ID NO:43), or
Ac-(N-Me)Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:44).

We have discovered that the rat and human GHRH receptor display different structure activity relations for the human GHRH (hGHRH) peptide. We have designed a series of truncated analogs of hGHRH. The analogs activates the GHRH receptor, but does not have the disadvantages of GHRH. An advantage of these truncated analogs is their improved metabolic stability. Further the truncated analogs may offer advantages with respect to prolonged or modified duration of action, decreased immunogenicity, selectivity/side effects and lower cost of production.

In the above structural formulas and throughout the present specification, the following terms have the indicated meanings:

The $C_{1-6}$-alkyl residues specified above are intended to include those alkyl residues of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are $C_{3-6}$-cycloalkyl such as cyclopropyl, cyclobutyl, cyclopentyl and cyclohexyl.

The $C_{1-6}$-alkoxy residues specified above are intended to include those alkoxy residues of the designated length in either a linear or branched or cyclic configuration. Examples of linear alkyloxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

In the present context, the term "aryl" is intended to include aromatic rings, such as carbocyclic and heterocyclic aromatic rings selected from the group consisting of phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrazinyl, or isothiazolyl.

Aryl is preferably phenyl, thienyl, imidazolyl, pyridyl, indolyl, oxadiazole, quinoline or naphthyl.

The term "halogen" is intended to include chlorine (Cl), fluorine (F), bromine (Br) and iodine (I).

Certain of the above defined terms may occur more than once in the above formula I, and upon such occurence each term shall be defined independently of the other.

The compounds of the present invention may have one or more asymmetric centres and it is intended that stereoisomers, as separated, pure or partially purified stereoisomers or racemic mixtures thereof are included in the scope of the invention.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoracetic, sulfamic or fumaric acid.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences,* 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
| --- | --- |
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.1–500 mg/day, e.g. from about 5 to about 50 mg, such as about 10 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, prevention and treatment of osteoporosis, stimulation of the immune system, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the growth hormone releasing hormones of formula I, they may be useful in vitro tools for investigating the regulation of growth hormone release.

The compounds of Formula I are also useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

The compounds of Formula I can be administered to commercially important animals to increase their rate and extent of growth, and to increase milk production.

Accordingly, the present invention include within its scope pharmaceutical compositions comprising, as an active ingredient, at least one of the compounds of Formula I in association with a pharmaceutical carrier or diluent. Optionally, the pharmaceutical composition can comprise at least one of the compounds of Formula I combined with compounds exhibiting a different activity, e.g., an antibiotic or other pharmacologically active material.

A further use of the compounds of Formula I is in combination with other secretagogues like GHRP's, such as GHRP (2 or 6), growth hormone and its analogues or somatomedins including IGF-1 and IGF-2.

For the above indications, dosage will vary depending on the compound of Formula I employed, on the mode of administration and on the therapy desired. However, generally dose levels between 0.0001 to 100 mg/kg body weight daily are administered to patients and animals to obtain effective release of endogenous growth hormone.

The route of administration may be any route which affectively transports the active compound to the appropriate or desired site of action, such as oral or parenteral, the oral route being the preferred.

Any novel feature or combination of features described herein is considered essential to this invention.

Pharmacological Methods
EXAMPLES

Compounds of Formula I were evaluated in vitro for their efficacy and potency to stimulate the human GHRH receptor in cell lines stably expressing this receptor. Briefly, 80% confluent cells were scraped off and pelleted at 10,000×g for 10 min at 4° C.

1. For binding assay the cell pellet was homogenized in 10 mM Tris-acetate buffer (pH 7.4) and centrifuged at 50,000×g for 10 min at 4C. The pellet were rehomogenized in the same buffer and diluted to 200 ug membrane protein/ml. Assay consisted of 25 ul $^{125}$I-GHRH(1-29)NH$_2$ (200,000 cpm/tube), 900 ul Tris-acetate buffer and 25 ul 0.2% Tween 20. This mixture was incubated for 45 min at room temperature. The reaction was terminated by rapid filtration through GF/B filters pre-wetted with 0.5% PEI.

2. For Adenylyl cyclase assay the cell pellet was processed and assay performed as described previously for Dopamine D1 receptors in Pedersen et al., Eur. J. Pharmacol. 267, 85–93, 1994.

3. Compounds of Formula I were evaluated in vitro for their efficacy and potency to release growth hormone in primary rat somatotrophs. Rat primary somatotrophs were prepared essentially as described previously (Chen et al., Endocrinology 129, 3337–3342, 1991 and Chen et al., Endocrinology, 124, 2791–2798, 1989). Briefly, rats were killed by decapitation. The pituitary were quickly removed. The pituitaries were digested with 0.2% collagenase n 0.2% hyaluronidase in Hanks balanced salt solution. The cells were resuspended in Dulbecco@s modified eagles medium containing 0.37% NaHCO$_2$, 10% horse serum, 2.5% fetal calf serum, 1% nonessential amino acids, 1% glutamine and 1% pen/strep and adjusted to 1.5×10$^5$ cells/ml. One ml of this suspension was placed in each well of 24-well trays and left for 2–3 days before release experiments were performed.

On the day of the experiments, cells were washed twice with the above medium containing 25 mM HEPES, pH 7.4. Growth hormone release were initiated by addition of medium containing 25 mM HEPES and test compound. Incubation was carried out for 15 min at 37° C. After incubation growth hormone released to the medium was measured by a standard RIA assay.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

Abbrevations
TLC: thin layer chromatography
DMSO: dimethylsulfoxide
min: minutes
h: hours
Experimental Procedures
Method 1

Linear peptides were synthesized with an ABI 431A peptide synthesizer using standard protocols according to the Fmoc SPPS strategy (as substantially described by Fields et al., *Int. J. Pept. Protein Res.* 35, 1990, 161) on Rink amide polystyrene resin [4-((4',2'-dimethoxyphenyl)-(Fmoc-amino)methyl)-phenoxy resin, e.g. Novabiochem, Bad Soden, Germany, cat.#01-64-0013]. The peptides were cleaved from resin using standard cleavage cocktails containing a mixture of trifluoroactic acid and common scavengers (e.g., a mixture of trifluoroacetic acid (4 mL), phenol (300 mg), ethanedithiol (0.10 mL), thioanisole (0.20 mL) and water (0.20 mL), or as substantially described in the "novabiochem catalog and Peptide Synthesis Handbook" 94/95 on pages S34 to 336 and in references 1 to 15 listed on page S39). Subsequently, the cleavage mixture was concentrated to 1 mL using a stream of nitrogen, and the crude peptides were precipitated from this oil with diethyl ether (45 mL), washed with diethyl ether (3 portions of 50 mL) and dried.

Purifications were performed by semipreparative HPLC using a Sep-Pak C18 cartridge (Waters part.# 51910). All purified peptides were characterized by at least one analytical HPLC chromatogram on a Waters 510 system equipped with a Vydac C18 column (5 to 60% acetonitrile in water, 42° C., 0.1 M ammonium sulfate, pH adjusted to 2.5 with 4 M sulfuric acid, 50 min) and plasma desorption mass spectroscopy.

The following peptides were prepared by method 1 (retention time $R_t$ using a gradient of 5 to 60% acetonitrile in water, 42° C., 0.1 M ammonium sulfate, pH adjusted to 2.5 with 4 M sulfuric acid, 50 min; calculated molecular mass, found molecular mass):

Asp-Ala-Tyr-Arg-Lys-Val-Leu-Ala-Gln-Leu-Ser-Ala-Arg-His-NH$_2$ [$R_t$=20.98 min] (SEQ ID NO:1)
Asp-Ala-Tyr-Arg-Lys-Val-Leu-Ala-Glu-Leu-Ser-Ala-Arg-His-NH$_2$ [$R_t$=21.93 min] (SEQ ID NO:12)
Ac-Asp-Ala-Tyr-Arg-Lys-Val-Leu-Ala-Gln-Leu-Ser-Ala-Arg-His-NH$_2$ [$R_t$=23.75 min]; calculated 1669.0, found 1669±2 (SEQ ID NO:2)
Ac-Asp-Ala-Tyr-Arg-Lys-Val-Leu-Ala-Glu-Leu-Ser-Ala-Arg-His-NH$_2$ [$R_t$=24.37 min]; calculated 1670.0, found 1669.2±2 (SEQ ID NO:12)
Ac-Asp-Ala-Tyr-Arg-Lys-Val-Leu-Ala-Gln-Leu-Ser-Ala-Lys-His-NH$_2$ [$R_t$=22.85 min]; calculated 1642.0, found 1640.7±2 (SEQ ID NO:25)
H-Tyr-Ala-Asp-Ala-Ile-Phe-Thr-Asp-Ala-Tyr-Arg-Lys-Val-Leu-Ala-Gln-Leu-Ser-Ala-Arg-His-NH$_2$ ($R_t$=29.33 min, M=2408±1) (SEQ ID NO:38)
Ac-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ ($R_t$=31.98 min, M=2701±3) (SEQ ID NO:39)
Ac-Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ ($R_t$=32.33 min, M=2771±3) (SEQ ID NO:40)
Ac-(N-Me)Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ ($R_t$=32.78 min, M=2784±3) (SEQ ID NO:44)

Method 2

Linear peptides were synthesized using standard protocols according to the Fmoc SPPS strategy (as substantially described by Fields et al., *Int. J. Pept. Protein Res.* 35, 1990, 161) and to method 1 on either an Abimed 422 MPS, Milligen 9050 continuous flow, or ACT Model 90 2 vessel machine. The peptides were cleaved from resin using standard cleavage cocktails containing a mixture of trifluoroactic acid and common scavengers (similar to method 1, or as substantially described in the "novabiochem catalog and Peptide Synthesis Handbook" 94/95 on pages S34 to S36 and in references 1 to 15 listed on page S39). Subsequently, the cleavage mixture was concentrated, and the crude peptides were precipitated with diethyl ether and dried, similar to method 1.

Purifications were performed on a Gilson computer controlled HPLC or EM science 2 liter/min HPLC using a 15×50 cm Sep-tech column. All purified peptides were characterized by at least one analytical HPLC chromatogram (5 to 50% acetonitrile in water, 0.1% trifluoroacetic acid, 16 min) and laser desorption mass spectroscopy.

The following peptides were prepared by method 2 (retention time $R_t$ using a gradient of 5 to 50% acetonitrile in water, 0.1% trifluoroacetic acid, 16 min; molecular mass M+H of the singly protonated molecule):

Asp-Ala-Tyr-Arg-Lys-Val-Leu-Ala-Gln-Leu-Ser-Ala-Arg-His-NH$_2$ ($R_t$=9.13 min; M+H=1624) (SEQ ID NO:19)
Asp-Tyr-Arg-Lys-Val-Leu-Ala-Gln-Leu-Ser-Ala-Arg-His-NH$_2$ ($R_t$=10.66 min; M+H=1556) (SEQ ID NO:4)
Asp-Ala-Tyr-Arg-Ala-Val-Leu-Ala-Gln-Leu-Ser-Ala-Arg-His-NH$_2$ ($R_t$=10.84 min; M+H=1569) (SEQ ID NO:3)
Asp-Val-Leu-Ala-Gln-Leu-Ser-Ala-Arg-His-NH$_2$ ($R_t$=8.47 min; M+H=1108) (SEQ ID NO:10)
Asp-Lys-Val-Leu-Ala-Gln-Leu-Ser-Ala-Arg-His-NH$_2$ ($R_t$=8.03 min; M+H=1237) (SEQ ID NO:9)
Asp-Tyr-Arg-Lys-Val-Leu-Ala-Gln-Leu-Ser-Ala-Arg-His-NH$_2$ ($R_t$=8.12 min; M+H=1553) (SEQ ID NO:4)
Asp-Leu-Ala-Gln-Leu-Ser-Ala-Arg-His-NH$_2$ ($R_t$=5.92 min; M+H=1009) (SEQ ID NO:11)
Asp-Arg-Lys-Val-Leu-Ala-Gln-Leu-Ser-Ala-Arg-His-NH$_2$ ($R_t$=8.07 min; M+H=1391) (SEQ ID NO:8)
Asp-Ala-Tyr-Arg-Lys-Val-Leu-Ala-Gln-Leu-homoArg-His-NH$_2$ ($R_t$=9.07 min; M+H=1481) (SEQ ID NO:5)
Asp-Tyr-Arg-Ala-Val-Leu-Ala-Gln-Leu-homoArg-His-NH$_2$ ($R_t$=9.55 min; M+H=1352) (SEQ ID NO:7)
Asp-Ala-Tyr-Arg-Ala-Val-Leu-Ala-Gln-Leu-homoArg-His-NH$_2$ ($R_t$=9.70 min; M+H=1423) (SEQ ID NO:6)
Tyr-Ala-Asp-Ala-Ile-Phe-Thr-Gln-Ser-Tyr-Arg-Lys-Val-Leu-Ala-Gln-Leu-Ser-Ala-Arg-His-NH$_2$ ($R_t$=11.77 min; M+H=2436) (SEQ ID NO:45)

Method 3

Cyclic peptides by sidechain to sidechain cyclization from an amino to a carboxy group were synthesized using 4-methylbenzhydryl (MBHA) polystyrene resin and an ABI 430 peptide synthesizer employing standard protocols according to the Boc SPPS strategy (e.g, as substantially described by Stewart and Young, *Solid Phase Peptide Synthesis*, 2nd ed., Rockford, Ill., USA, 1976). In general, sidechain functionalities intended for cyclization were protected using a base-labile protecting group (Fmoc-protection for amino groups, fluorenylmethylester-protection for carboxy groups, as described in T. W. Greene, P. G. M. Wuts, *Protective Groups in Organic Synthesis*, 2nd ed., J. Wiley & Sons, New York 1991, or in the "novabiochem catalog and Peptide Synthesis Handbook" 94/95 on pages S29 to S33 and in references 1 to 16 listed on page S33); other sidechain functionalities were protected using standard, hydrofluoric acid labile protecting groups suitable for Boc peptide synthesis (e.g., as described by Stewart and Young, *Solid Phase Peptide Synthesis*, 2nd ed., Rockford, Ill., USA, 1976). For cyclization of peptides via the sidechain functionality of lysine or ornithine, the amino group in the sidechain can be acylated with an Fmoc protected spacer amino acid (e.g., FmocGly); subsequently, the amino group of the spacer amino acid can be used for formation of the amide bond with the sidechain functionality of glutamic acid or aspartic acid.

After formation of the cyclic structure and removal of the N-terminal Boc group, further synthesis and final cleavage are carried out under standard conditions for Boc SPPS strategy.

The crude peptide was dried and purified by HPLC on a 20 mm×250 mm column packed with 7μ C-18 silica which was preequilibrated with 15% CH$_3$CN in 0.05 M (NH$_4$)$_2$SO$_4$, which was adjusted to pH 2.5 with 4 M H$_2$SO$_4$. The crude peptide was dissolved in 2 mL 70% CH$_3$CN/0.1% TFA in H$_2$O and diluted to 100 mL with H$_2$O. This solution was divided into two equal portions and each of them were injected on the column in two separate runs. The column was eluted with a gradient of 15%–25% CH$_3$CN in 0.05 M (NH$_4$)$_2$SO$_4$, pH 2.5 at 10 mL/min during 47 min at 40° C. The peptide-containing fractions were collected, diluted with 3 volumes of H$_2$O and applied to a Sep-Pak® C18 cartrtidge (Waters part. #:51910) which was equilibrated with 0.1% TFA/H$_2$O. The peptide was eluted from the Sep-Pak® cartridge with 70% CH$_3$CN/0.1% TFA/H$_2$O and isolated from the eluate after dilution with water.

The final product obtained was characterized by analytical RP-HPLC (retention time) and by plasma desorption mass spectrometry (molecular mass). Mass spectrometry ageed with the expected structure within the experimental error of the method.

The RP-HPLC analysis was performed using UV-detection at 214 nm and a Vydac 218TP54 4.6 mm×250 mm 5μ C-18 silica column (the Separations Group, Hesperia) which was eluted at 1 mL/min at 42 ° C. Two different elution conditions were used:

A1: The column was equilibrated with 5% CH$_3$CN in a buffer consisting of 0.1 M (NH$_4$)$_2$SO$_4$, which was adjusted to pH 2.5 with 4 M H$_2$SO$_4$, and eluted with a gradient of 5% to 60% CH$_3$CN in the same buffer during 50 min.

B1: The column was equilibrated with 5% CH$_3$CN/0.1% TFA/H$_2$O and eluted by a gradient of 5% CH$_3$CN/0.1% TFA/H$_2$O to 60% CH$_3$CN/0.1% TFA/H$_2$O during 50 min.

Cyclo (Asp$^2$-[Gly]-Orn$^6$)-Ac-Asp-Asp-Ile-Phe-Thr-Orn-Ala-Tyr-Arg-Lys-Val-Leu-Ala-Gln-Leu-Ser-Ala-Arg-Lys-Leu-Leu-Gln-His-NH$_2$ (R$_t$ A1=33.11 min, R$_t$ B1=34.65 min, M=2781±3) (SEQ ID NO:41)

Cyclo (Asp$^6$-[Gly]-Orn$^{10}$)-Ac-Asp-Ala-Ile-Phe-Thr-Asp-Ala-Tyr-Arg-Orn-Val-Leu-Ala-Gln-Leu-Ser-Ala-Arg-Lys-Leu-Leu-Gln-His-NH$_2$ (R$_t$ A1=34.30 min, R$_t$ B1=36.28 min, M=2723±3) (SEQ ID NO:42)

Cyclo (Asp$^{10}$-[Gly]-Orn$^{14}$)-Ac-Asp-Ala-Ile-Phe-Thr-Asp-Ala-Tyr-Arg-Asp-Val-Leu-Ala-Orn-Leu-Ser-Ala-Arg-Lys-Leu-Leu-Gln-His-NH$_2$ (R$_t$ A1=33.90 min, R$_t$ B1=35.72 min, M=2710±3) (SEQ ID NO:43)

Cyclo(Asp$^1$-[Gly]-Orn$^5$)-Asp-Ala-Tyr-Arg-Orn-Val-Leu-Ala-Gln-Leu-Ser-Ala-Arg-His-NH$_2$ (R$_t$=23.17 min; M=1652) (SEQ ID NO:22)

Abbreviations and definitions: Pen=penicillamine, Orn=ornithine, Nleu=Norleucine, homoarg=homoarginine, SPPS=solid phase peptide synthesis, Fmoc=fluorenylmethoxycarbonyl; Boc=tert.butyloxycarbonyl Cyclo(Glu$^9$-Lys$^{13}$) means that the sidechains of Glu$^9$ and Lys$^{13}$ are connected by an amide bond under formation of a cyclic structure;

Cyclo(Lys$^5$-Glu$^9$) means that the sidechains of Lys$^5$ and Glu$^9$ are connected by an amide bond under formation of a cyclic structure;

Cyclo(Asp$^1$-[Gly]-Orn$^5$) means that the sidechain of Asp$^1$ is connected by an amide bond to the amino group of Gly by an amide bond and that the carboxylate of Gly is connected by an amide bond to the amino group of Orn$^5$ under formation of a cyclic structure;

Cyclo(Asp$^2$-[Gly]-Orn$^6$) means that the sidechain of Asp$^2$ is connected by an amide bond to the amino group of Gly by an amide bond and that the carboxylate of Gly is connected by an amide bond to the amino group of Orn$^6$ under formation of a cyclic structure;

Cyclo(Asp$^6$-[Gly]-Orn$^{10}$) means that the sidechain of Asp$^6$ is connected by an amide bond to the amino group of Gly by an amide bond and that the carboxylate of Gly is connected by an amide bond to the amino group of Orn$^{10}$ under formation of a cyclic structure;

Cyclo(Asp$^{10}$-[Gly]-Orn$^{14}$) means that the sidechain of Asp$^{10}$ is connected by an amide bond to the amino group of Gly by an amide bond and that the carboxylate of Gly is connected by an amide bond to the amino group of Orn$^{14}$ under formation of a cyclic structure;

Cyclo(Lys$^4$-Glu$^8$) means that the sidechains of Lys$^4$ and Glu$^8$ are connected by an amide bond under formation of a cyclic structure;

Cyclo(Orn$^2$-[COCH$_2$]-Pen$^6$) means that the sidechain of Orn$^2$ is connected by an amide bond to the carboxylate of an acetic acid moiety and that the methylene group of the acetic acid moiety is connected by a thioether bond to the sulfur atom of Pen$^6$ under formation of a cyclic structure;

Cyclo(Lys$^3$-Glu$^7$) means that the sidechains of Lys$^3$ and Glu$^7$ are connected by an amide bond under formation of a cyclic structure;

Cyclo(Lys$^2$-Glu$^6$) means that the sidechains of Lys$^2$ and Glu$^6$ are connected by an amide bond under formation of a cyclic structure;

Cyclo(Glu$^1$-Lys$^5$) means that the sidechains of Glu$^1$ and Lys$^5$ are connected by an amide bond under formation of a cyclic structure.

We claim:

1. A compound of formula I

wherein

Z and w are independently 0 or 1,

A and D are independently a non-proteinogenic or proteinogenic alpha amino acid residue of formula II

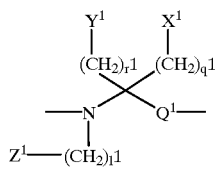

formula II wherein $Q^1$ is —CH$_2$— or —CO—, $l^1$, $q^1$ and $r^1$ are independently 0, 1, 2, 3, 4, 5, or 6, $X^1$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^1$, $Y^1$ is hydrogen, a $C_{1-6}$-alkyl group, or a valence bond to $X^1$ or $Z^1$ $Z^1$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^1$, B, C, E, F are independently (a) a non-proteinogenic or proteinogenic alpha amino acid residue of formula III

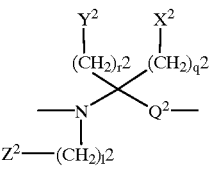

formula III wherein $Q^2$ is —CH$_2$— or —CO—, $l^2$, $q^2$ and $r^2$ are independently 0, 1, 2, 3, 4, 5, or 6, $X^2$ is hydrogen; or a $C_{1-6}$-alkyl group optionally substituted with a halogen, hydroxy, $C_{1-6}$alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^2$, $Y^2$ is hydrogen, a $C_{1-6}$-alkyl group, or a valence bond to $X^2$ or $Z^2$, $Z^2$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^2$;

or (b) the residues of any of the following, non-proteinogenic amino acids (R- and S- isomer for chiral amino acids) dehydroalanine, anthranilic acid, 3-aminobenzoic acid, 4-aminobenzoic acid, 4-aminobutyric acid, beta-alanine, 3-amino-1,2,4-triazole-5-carboxylic acid, 1,2,3,4-tetrahyroisoquinoline-3-carboxylic acid, aminobiphenylcarboxylic acids, pipecolic acid, nipecotinic acid, isonipecotinic acid, statine, 4-amino-3-hydroxybutyric acid, aminohexanoic acid, 2-amino-2-thiazoline-4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans-2-aminocyclohexanecarboxylic acid, 4-aminomethylcyclohexanecarboxylic acid, 4-aminomethylbenzoic acid, aminonaphthoic acid, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid;

G is a non-proteinogenic or proteinogenic alpha amino acid residue of formula IV

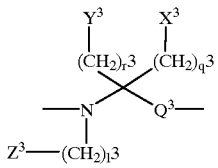

formula IV wherein $Q^3$ is —$CH_2$— or —CO—, $l^3$, $q^3$ and $r^3$ are independently 0, 1, 2, 3, 4, 5, or 6, $X^3$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^3$, $Y^3$ is hydrogen, a $C_{1-6}$-alkyl group, or a valence bond to $X^3$ or $Z^3$, $Z^3$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^3$, M is (a) an amino acid residue, a dipeptide residue, a tripeptide residue, a tetrapeptide residue, a pentapeptide residue, a hexapeptide residue, a heptapeptide residue, a octapeptide residue, a nonapeptide residue, a decapeptide residue, a undecapeptide residue, a dodecapeptide residue or a tredecapeptide residue, wherein the amino acid residues are independently any non-proteinogenic or proteinogenic alpha amino acid residue of formula V

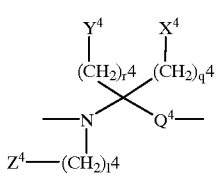

formula V wherein $Q^4$ is —$CH_2$— or —CO—, $l^4$, $q^4$ and $r^4$ are independently 0, 1, 2, 3, 4, 5, or 6, $X^4$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^4$, $Y^4$ is hydrogen, a $C_{1-6}$-alkyl group, or a valence bond to $X^4$ or $Z^4$, $Z^4$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^4$;

or (b) the residues of any of the following, non-proteinogenic amino acids (R- and S- isomer for chiral amino acids) dehydroalanine, anthranilic acid, 3-aminobenzoic acid, 4-aminobenzoic acid, 4-aminobutyric acid, beta-alanine, 3-amino-1,2,4-triazole-5-carboxylic acid, 1,2,3,4-tetrahyroisoquinoline-3-carboxylic acid, aminobiphenylcarboxylic acids, pipecolic acid, nipecotinic acid, isonipecotinic acid, statine, 4-amino-3-hydroxybutyric acid, aminohexanoic acid, 2-amino-2-thiazoline-4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans-2-aminocyclohexanecarboxylic acid, 4-aminomethylcyclohexanecarboxylic acid, 4-aminomethylbenzoic acid, aminonaphthoic acid, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid;

N is (a) an amino acid residue, a dipeptide residue, an oligopeptide residue or an oligoamide residue which is between 1 to 10 amino acid residues long wherein the amino acid residues independently are any non-proteinogenic or proteinogenic alpha-amino acid residue of formula VI

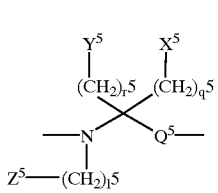

formula VI wherein $Q^5$ is —$CH_2$— or —CO—, $l^5$, $q^5$ and $r^5$ are independently 0, 1, 2, 3, 4, 5, or 6, $X^5$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^5$, $Y^5$ is hydrogen, a $C_{1-6}$-alkyl group, or a valence bond to $X^5$ or $Z^5$, $Z^5$ is hydrogen; or a $C_{1-6}$-alkyl group optionally substituted with a halogen, hydroxy, $C_{1-6}$-alkoxy, aryloxy, mercapto, $C_{1-6}$-alkylmercapto, arylmercapto, guanidino, amidino, amino, $C_{1-6}$-dialkylamino, $C_{1-6}$-alkylamino, carboxy, carbamoyl, aryl group; or an aryl group optionally substituted with a hydroxy, halogen, mercapto, carboxy, carbamoyl, amino, $C_{1-6}$-dialkylamino, $C_{1-6}$-alkylamino, amidino, guanidino, $C_{1-6}$-alkoxy, $C_{1-6}$-alkyl group; or a valence bond to $Y^5$; or (b) the residues of any of the following, non-proteinogenic amino acids (R- and S- isomer for chiral amino acids) dehydroalanine, anthranilic acid, 3-aminobenzoic acid, 4-aminobenzoic acid, 4-aminobutyric acid, beta-alanine, 3-amino-1,2,4-triazole-5-carboxylic acid, 1,2,3,4-tetrahyroisoquinoline-3-carboxylic acid, aminobiphenylcarboxylic acids, pipecolic acid, nipecotinic acid, isonipecotinic acid, statine, 4-amino-3-hydroxybutyric acid, aminohexanoic acid, 2-amino-2-thiazoline-4-carboxylic acid, 1,2,3,4-tetrahyronorharman-3-carboxylic acid, 3-amino-3-methylbenzoic acid, 3-aminomethylbutanoic acid, 5-aminopentanoic acid, 2-aminothiazoleacetic acid, 2-aminothiopheneacetic acid, cis- and trans-2-aminocyclohexanecarboxylic acid, 4-aminomethylcyclohexanecarboxylic acid, 4-aminomethylbenzoic acid, aminonaphthoic acid, aminopenicillanic acid, 3-aminopyrazole-4-carboxylic acid, 2-amino-4-pentenoic acid, 2-aminothiopheneacetic acid, 3-aminobutyric acid, aminolevulinic acid, 8-aminocaprylic acid; the total number of amino acid residues of N and M is equal to or less than 17, x and y are independently 0 or 1; when the sidechain of an amino acid residue of either M, A, B, C, D, E, F, G, or N contains an amino group, it can optionally be connected to a sidechain of an amino acid residue of M, A, B, C, D, E, F, G, or N containing a carboxylic acid group in order to generate a linkage of formula VII

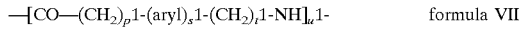   formula VII wherein $u^1$ and $s^1$ are independently 0, 1, or 2, $t^1$ and $p^1$ are independently 0, 1, 2, 3, 4, 5, 6, 7, or 8;
when a sidechain of an amino acid residue of either M, A, B, C, D, E, F, G, or N contains a mercapto group, it can optionally be connected to a side-chain of an amino acid residue of either M, A, B, C, D, E, F, G, or N containing an amino group in order to generate a linkage of formula VIII

   formula VIII wherein $p^2$ is 1, 2, 3, 4, or 5, $s^2$ is independently 0 or 1;
when a sidechain of an amino acid residue of either M, A, B, C, D, E, F, G, or N contains a mercapto group, it can optionally be connected to the methylene group of a dehydroalanine residue of either M, A, B, C, D, E, F, G, or N in order to generate a thioether linkage;
when the sidechains of two or more amino acid residues of M, A, B, C, D, E, F, G, or N contain a mercapto group, they can optionally be connected in order to generate a disulfide linkage;

K is $W^1$—$(CH_2)_v1$-CO—, or $W^2$—$(CH_2)_v2$-NH—CO—, or $W^3$—$(CH_2)_v3$-O—CO—, or $W^4$—$(CH_2)_v4$-SO_2—, wherein $v^1$, $v^2$, $V^3$ and $v^4$ independently are 0, 1, 2, 3, 4, 5, or 6, $W^1$, $W^2$, $W^3$ and $W^4$ independently are hydrogen, hydroxy, $C_{1-6}$-alkyl, aryl, or amino group; or a linkage to a sidechain of an amino acid residue of M, A, B, C, D, E, F, G, or N containing a carboxylic acid group of formula IX

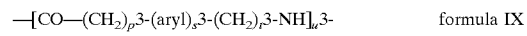   formula IX wherein $u^3$ and $s^3$ are independently 0, 1, or 2, $t^3$ and $p^3$ are independently 0, 1, 2, 3, 4, 5, 6, 7, or 8; or a linkage joining K and L of formula X

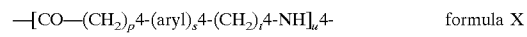   formula X wherein $u^4$ and $s^4$ are independently 0, 1, or 2, $t^4$ and $p^4$ are independently 0, 1, 2, 3, 4, 5, 6, 7, or 8;

L is —O—$(CH_2)_{p}5$-$W^5$ wherein $p^5$ is 0, 1, 2, 3, 4, 5, or 6, $W^5$ is hydrogen, hydroxy, $C_{1-6}$-alkyl, aryl, or amino group; or L is

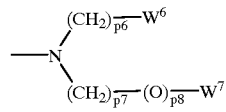

wherein $p^6$ and $p^7$ are independently 0, 1, 2, 3, 4, 5, or 6, $p^8$ is 0 or 1, $W^6$ and $W^7$ are independently hydrogen, hydroxy, $C_{1-6}$-alkyl, aryl, amino group, or a valence bond; or a linkage to an amino group in the sidechain of an amino acid residue of M, A, B, C, D, E, F, G, or N of formula XI

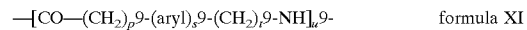   formula XI wherein $u^9$ and $s^9$ are independently 0, 1 or 2, $t^9$ and $p^9$ are independently 0, 1, 2, 3, 4, 5, 6, 7, or 8; or a pharmaceutically acceptable salt thereof.

2. The compound of claim 1 wherein A is a non-proteinogenic or proteinogenic amino acid of formula II formula II

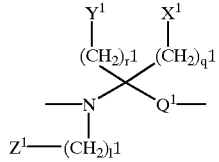

wherein $Q^1$ is —$CH_2$— or —CO—, $l^1$ and $r^1$ are 0, $q^1$ is 0, 1, 2, 3, or 4, $X^1$ is hydrogen, isopropyl, tert butyl, phenyl, cyclopropyl, cyclohexyl, 2-hydroxyethyl, or amino, $Y^1$ is hydrogen, or methyl, $Z^1$ is hydrogen.

3. The compound of claim 2 wherein A is the residue of leucine, isoleucine, valine, phenylalanine, cyclohexylalanine or homophenylalanine.

4. The compound of claim 2 wherein A is the residue of leucine.

5. The compound of claim 1 wherein B is
(a) a non-proteinogenic or proteinogenic alpha amino acid residue of formula III

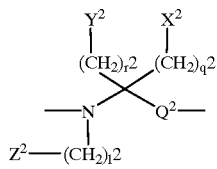

formula III wherein $Q^2$ is —CH$_2$— or —CO—, $l^2$ and $r^2$ are 0, $q^2$ is 0, 1, 2, 3, or 4, $X^2$ is hydrogen, phenyl, amino, guanidino, hydroxy, isopropyl, carboxy $Y^2$ is hydrogen, or methyl, $Z^2$ is hydrogen, or (b) the residue of any of the following, non-proteinogenic amino acids; dehydroalanine, anthranilic acid, 3-aminobenzoic acid, 4-aminobenzoic acid, 4-aminobutyric acid, beta-alanine, cis- and trans-2-aminocyclohexanecarboxylic acid, 4-aminomethylcyclohexanecarboxylic acid or 4-aminomethylbenzoic acid.

6. The compound of claim 5, wherein B is the residue of glycine, alanine, serine, lysine, ornithine, arginine, glutamic acid or aspartic acid.

7. The compound of claim 5, wherein B is the residue of alanine.

8. The compound of claim 1 wherein C is a non-proteinogenic or proteinogenic alpha amino acid residue of formula III

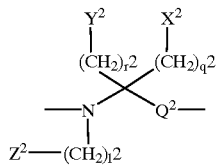

formula III wherein $Q^2$ is —CH$_2$— or —CO—, $l^2$ and $r^2$ are 0, $q^2$ is 0, 1, 2, 3, or 4, $X^2$ is hydrogen, imidazolyl, phenyl, amino, hydroxy, isopropyl, carboxy, aminocarbonyl, or guanidino, $Y^2$ is hydrogen or methyl, $Z^2$ is hydrogen.

9. The compound of claim 5 wherein C is the residue of lysine, glutamine, glutamic acid, asparagine, aspartic acid, arginine, ornithine, serine or histidine.

10. The compound of claim 5 wherein C is the residue of glutamine or ornithine.

11. The compound of claim 1 wherein D is a non-proteinogenic or proteinogenic amino acid of formula II

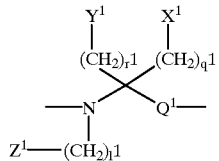

formula II wherein $Q^1$ is —CH$_2$— or —CO—, $l^1$ and $r^1$ are 0, $q^1$ is 0, 1, 2, 3, or 4, $X^1$ is hydrogen, isopropyl, tert. butyl, phenyl, cyclopropyl, cyclohexyl, 2-hydroxyethyl, or amino, $Y^1$ is hydrogen, or methyl, $Z^1$ is hydrogen.

12. The compound of claim 11, wherein D is the residue of leucine, isoleucine, valine, phenylalanine, cyclohexylalanine or homophenylalanine.

13. The compound of claim 11, wherein D is the residue of leucine.

14. The compound of claim 1 wherein E is
(a) a non-proteinogenic or proteinogenic alpha amino acid residue of formula III

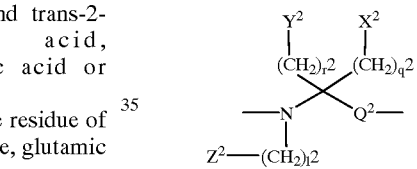

formula III wherein $Q^2$ is —CH$_2$— or —CO—, $l^2$ and $r^2$ are 0, $q^2$ is 0, 1, 2, 3, or 4, $X^2$ is hydrogen, phenyl, amino, guanidino, hydroxy, isopropyl, carboxy, $Y^2$ is hydrogen, or methyl, $Z^2$ is hydrogen, or (b) the residue of any of the following, non-proteinogenic amino acids; dehydroalanine, anthranilic acid, 3-aminobenzoic acid, 4-aminobenzoic acid, 4-aminobutyric acid, beta-alanine, cis- and trans-2-aminocyclohexanecarboxylic acid, 4-aminomethylcyclohexanecarboxylic acid or 4-aminomethylbenzoic acid.

15. The compound of claim 14, wherein E is the residue of glycine, alanine, serine, threonine, tyrosine, lysine, ornithine, glutamic acid, aspartic acid, homoarginine or arginine.

16. The compound of claim 14, wherein E is the residue of serine.

17. The compound of claim 1 wherein z is 1 and F is a non-proteinogenic or proteinogenic alpha amino acid residue of formula III

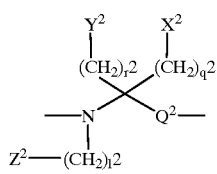

formula III wherein
$Q^2$ is —$CH_2$— or —CO—,
$l^2$ and $r^2$ are 0, $q^2$ is 0, 1, 2, 3, or 4,
$X^2$ is hydrogen, phenyl, amino, hydroxy, isopropyl, carboxy, aminocarbonyl, or guanidino,
$Y^2$ is hydrogen or methyl,
$Z^2$ is hydrogen.

18. The compound of claim 17, wherein F is the residue of alanine, phenylalanine, glycine, serine, valine, lysine, glutamine, glutamic acid, asparagine, aspartic acid or arginine.

19. The compound of claim 17, wherein F is alanine.

20. The of claim 1 wherein G is a non-proteinogenic or proteinogenic amino acid residue of formula IV

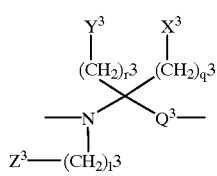

Formula IV wherein
$Q^3$ is —$CH_2$— or —CO—,
$l^3$ and $r^3$ are 0, $q^2$ is 0, 1, 2, 3, or 4,
$X^3$ is amino, methylamino, dimethylamino, amidino, benzamidino, guanidino, imidazolyl, hydroxy, aminocarbonyl,
$Y^3$ is hydrogen or methyl,
$Z^3$ is hydrogen.

21. The compound of claim 20, wherein G is the residue of arginine, lysine, glutamine, ornithine, histidine, serine or asparagine.

22. The compound of claim 20, wherein G is arginine.

23. The compound of claim 1, wherein M is the residue of valine, isoleucine, leucine, penicillamine, lysine, glutamic acid, glutamine, aspartic acid, arginine, alanine, cysteine, homocysteine, leucine, isoleucine, methionine, ornithine, phenylalanine or threonine.

24. The compound of claim 1, wherein M is valine.

25. The compound of claim 1, wherein M is a dipeptide residue and the amino acid residue in the aminoterminal position of the dipeptide residue is the residue of lysine, arginine, ornithine, histidine, glutamine, alanine, glutamic acid, aspartic acid, asparagine, cysteine or serine, and the amino acid residue in the second position of the dipeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

26. The compound of claim 1, wherein M is a dipeptide residue and the amino acid residue in the aminoterminal position of the dipeptide residue is the residue of lysine, aspartic acid or ornithine, and the amino acid residue in the second position of the dipeptide residue is the residue of valine.

27. The compound of claim 1, wherein M is a tripeptide residue and the amino acid residue in the aminoterminal position of the tripeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the second position of the tripeptide residue is the residue of lysine, arginine, ornithine, histidine, glutamine, alanine, glutamic acid, aspartic acid, asparagine, cysteine or serine, the amino acid residue in the third position of the dipeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

28. The compound of claim 1, wherein M is a tripeptide residue and the amino acid residue in the amino terminal position of the tripeptide residue is the residue of arginine, the amino acid residue in the second position of the tripeptide residue is the residue of lysine, ornithine or aspartic acid, the amino acid residue in the third position of the dipeptide residue is the residue of valine.

29. The compound of claim 1, wherein M is a tetrapeptide residue and the amino acid residue in the amino terminal position of the tetrapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the second position of the tetrapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the third position of the tetrapeptide residue is the residue of lysine, arginine, ornithine, histidine, glutamine, alanine, glutamic acid, aspartic acid, asparagine, cysteine or serine, the amino acid residue in the fourth position of the tetrapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

30. The compound of claim 1, wherein M is a tetrapeptide residue and the amino acid residue in the amino terminal position of the tetrapeptide residue is the residue of tyrosine, the amino acid residue in the second position of the tetrapeptide residue is the residue of arginine, the amino acid residue in the third position of the tetrapeptide residue is the residue of lysine, ornithine or aspartic acid, the amino acid residue in the fourth position of the tetrapeptide residue is the residue of valine.

31. The compound of claim 1, wherein M is a pentapeptide residue and the amino acid residue in the amino terminal position of the pentapeptide residue is the residue of serine, alanine, cysteine, threonine, lysine, valine, asparagine, aspartic acid, glutamine or glutamic acid, the amino acid residue in the second position of the pentapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the third position of the pentapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the fourth position of the pentapeptide residue is the residue of lysine, arginine, ornithine, histidine, glutamine, alanine, glutamic acid, aspartic acid, asparagine, cysteine or serine, the amino acid residue in the fifth position of the pentapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

32. The compound of claim 1, wherein M is a pentapeptide residue and the amino acid residue in the amino terminal position of the pentapeptide residue is the residue of alanine, the amino acid residue in the second position of the pentapeptide residue is the residue of tyrosine, the amino acid residue in the third position of the pentapeptide residue is the residue of arginine, the amino acid residue in the fourth position of the pentapeptide residue is the residue of lysine, ornithine or aspartic acid, the amino acid residue in the fifth position of the pentapeptide residue is the residue of valine.

33. The compound of claim 1, wherein M is a hexapeptide residue and the amino acid residue in the aminoterminal position of the hexapeptide residue is the residue of asparagine, aspartic acid, glutamine, glutamic acid, serine, lysine, alanine, threonine, cysteine or ornithine, the amino acid residue in the second position of the hexapeptide residue is the residue of serine, alanine, cysteine, threonine, lysine, valine, asparagine, aspartic acid, glutamine or glutamic acid, the amino acid residue in the third position of the hexapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the fourth position of the hexapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the fifth position of the hexapeptide residue is the residue of lysine, arginine, ornithine, histidine, glutamine, alanine, glutamic acid, aspartic acid, asparagine, cysteine or serine, ornithine or aspartic acid, the amino acid residue in the sixth position of the hexapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

34. The compound of claim 1, wherein M is a hexapeptide residue and the amino acid residue in the aminoterminal position of the hexapeptide residue is the residue of aspartic acid, glutamine or ornithine, the amino acid residue in the second position of the hexapeptide residue is the residue of alanine, the amino acid residue in the third position of the hexapeptide residue is the residue of tyrosine, the amino acid residue in the fourth position of the hexapeptide residue is the residue of asparagine, the amino acid residue in the fifth position of the hexapeptide residue is the residue of lysine, ornithine or aspartic acid, the amino acid residue in the sixth position of the hexapeptide residue is the residue of valine.

35. The compound of claim 1, wherein M is a heptapeptide residue and the amino acid residue in the aminoterminal position of the heptapeptide is the residue of threonine, serine, lysine, methionine, leucine, isoleucine, alanine, asparagine, glutamine, aspartic acid, glutamic acid, cysteine or histidine, the amino acid residue in the second position of the heptapeptide residue is the residue of asparagine, aspartic acid, glutamine, glutamic acid, serine, lysine, alanine, threonine, cysteine or ornithine, the amino acid residue in the third position of the heptapeptide residue is the residue of serine, alanine, cysteine, threonine, lysine, valine, asparagine, aspartic acid, glutamine or glutamic acid, the amino acid residue in the fourth position of the heptapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the fifth position of the heptapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the sixth position of the heptapeptide residue is the residue of lysine, arginine, ornithine, histidine, glutamine, alanine, glutamic acid, aspartic acid, asparagine, cysteine or serine, the amino acid residue in the seventh position of the heptapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

36. The compound of claim 1, wherein M is a heptapeptide residue and the amino acid residue in the aminoterminal position of the heptapeptide is the residue of threonine, the amino acid residue in the second position of the heptapeptide residue is the residue of aspartic acid, glutamine or ornithine, the amino acid residue in the third position of the heptapeptide residue is the residue of alanine, the amino acid residue in the fourth position of the heptapeptide residue is the residue of tyrosine, the amino acid residue in the fifth position of the heptapeptide residue is the residue of arginine, the amino acid residue in the sixth position of the heptapeptide residue is the residue of lysine, ornithine or aspartic acid, the amino acid residue in the seventh position of the heptapeptide residue is the residue of valine.

37. The compound of claim 1, wherein M is an octapeptide residue and the amino acid residue in the aminoterminal position of the octapeptide residue is the residue of phenylalanine, tyrosine, tryptophan, histidine, 1-naphthylalanine, 2-naphthylalanine, cyclohexylalanine or lysine, the amino acid residue in the second position of the octapeptide residue is the residue of threonine, serine, lysine, methionine, leucine, isoleucine, alanine, asparagine, glutamine, aspartic acid, glutamic acid, cysteine or histidine, the amino acid residue in the third position of the octapeptide residue is the residue of asparagine, aspartic acid, glutamine, glutamic acid, serine, lysine, alanine, threonine, cysteine or ornithine, the amino acid residue in the fourth position of the octapeptide residue is the residue of serine, alanine, cysteine, threonine, lysine, valine, asparagine, aspartic acid, glutamine or glutamic acid, the amino acid residue in the fifth position of the octapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the sixth position of the octapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the seventh position of the octapeptide residue is the residue of lysine, arginine, ornithine, histidine, glutamine, alanine, glutamic acid, aspartic acid, asparagine, cysteine or serine, the amino acid residue in the eighth position of the octapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

38. The compound of claim 1, wherein M is an octapeptide residue and the amino acid residue in the aminoterminal position of the octapeptide residue is the residue of phenylalanine, the amino acid residue in the second position of the octapeptide residue is the residue of threonine, the amino acid residue in the third position of the octapeptide residue is the residue of aspartic acid, glutamine or ornithine, the amino acid residue in the fourth position of the octapeptide residue is the residue of alanine, the amino acid residue in the fifth position of the octapeptide residue is the residue of tyrosine, the amino acid residue in the sixth position of the octapeptide residue is the residue of arginine, the amino acid residue in the seventh position of the octapeptide residue is the residue of lysine, ornithine or aspartic acid, the amino acid residue in the eighth position of the octapeptide residue is the residue of valine.

39. The compound of claim 1, wherein M is a nonapeptide residue and the amino acid residue in the aminoterminal position of the nonapeptide residue is the residue of isoleucine, leucine, valine, alanine, threonine, phenylalanine or methionine, the amino acid residue in the second position of the nonapeptide residue is the residue of phenylalanine, tyrosine, tryptophan, histidine, 1-naphthylalanine, 2-naphthylalanine, cyclohexylalanine or lysine, the amino acid residue in the third position of the nonapeptide residue is the residue of threonine, serine, lysine, methionine, leucine, isoleucine, alanine, asparagine, glutamine, aspartic acid, glutamic acid, cysteine or histidine, the amino acid residue in the fourth position of the nonapeptide residue is the residue of asparagine, aspartic acid, glutamine, glutamic acid, serine, lysine, alanine, threonine, cysteine or ornithine, the amino acid residue in the fifth position of the nonapeptide residue is the residue of serine, alanine, cysteine, threonine, lysine, valine, asparagine, aspartic acid, glutamine or glutamic acid, the amino acid residue in the sixth position of the nonapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the seventh position of the nonapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the eighth position of the nonapeptide residue is the residue of lysine, arginine, ornithine, histidine, glutamine, alanine, glutamic acid, aspartic acid, asparagine, cysteine or serine, the amino acid residue in the ninth position of the nonapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

40. The compound of claim 1, wherein M is a nonapeptide residue and the amino acid residue in the aminoterminal position of the nonapeptide residue is the residue of isoleucine, the amino acid residue in the second position of the nonapeptide residue is the residue of phenylalanine, the amino acid residue in the third position of the nonapeptide residue is the residue of threonine, the amino acid residue in the fourth position of the nonapeptide residue is the residue of aspartic acid, glutamine or ornithine, the amino acid residue in the fifth position of the nonapeptide residue is the residue of alanine, the amino acid residue in the sixth position of the nonapeptide residue is the residue of tyrosine, the amino acid residue in the seventh position of the nonapeptide residue is the residue of arginine, the amino acid residue in the eighth position of the nonapeptide residue is the residue of lysine, ornithine or aspartic acid, the amino acid residue in the ninth position of the nonapeptide residue is the residue of valine.

41. The compound of claim 1, wherein M is a decapeptide residue and the amino acid residue in the aminoterminal position of the decapeptide residue is the residue of alanine, valine, serine, leucine, lysine, threonine, glycine, glutamine, asparagine or histidine, the amino acid residue in the second position of the decapeptide residue is the residue of isoleucine, leucine, valine, alanine, threonine, phenylalanine or methionine, the amino acid residue in the third position of the decapeptide residue is the residue of phenylalanine, tyrosine, tryptophan, histidine, 1-naphthylalanine, 2-naphthylalanine, cyclohexylalanine or lysine, the amino acid residue in the fourth position of the decapeptide residue is the residue of threonine, serine, lysine, methionine, leucine, isoleucine, alanine, asparagine, glutamine, aspartic acid, glutamic acid, cysteine or histidine, the amino acid residue in the fifth position of the decapeptide residue is the residue of asparagine, aspartic acid, glutamine, glutamic acid, serine, lysine, alanine, threonine, cysteine or ornithine, the amino acid residue in the sixth position of the decapeptide residue is the residue of serine, alanine, cysteine, threonine, lysine, valine, asparagine, aspartic acid, glutamine or glutamic acid, the amino acid residue in the seventh position of the decapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the eighth position of the decapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the ninth position of the decapeptide residue is the residue of lysine, arginine, ornithine, histidine, glutamine, alanine, glutamic acid, aspartic acid, asparagine, cysteine or serine, the amino acid residue in the tenth position of the decapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

42. The compound of claim 1, wherein M is a decapeptide residue and the amino acid residue in the aminoterminal position of the decapeptide residue is the residue of alanine or asparagine, the amino acid residue in the second position of the decapeptide residue is the residue of isoleucine, the amino acid residue in the third position of the decapeptide residue is the residue of phenylalanine, the amino acid residue in the fourth position of the decapeptide residue is the residue of threonine, the amino acid residue in the fifth position of the decapeptide residue is the residue of aspartic acid, glutamine or ornithine, the amino acid residue in the sixth position of the decapeptide residue is the residue of alanine, the amino acid residue in the seventh position of the decapeptide residue is the residue of tyrosine, the amino acid residue in the eighth position of the decapeptide residue is the residue of arginine, the amino acid residue in the ninth position of the decapeptide residue is the residue of lysine, ornithine or aspartic acid, the amino acid residue in the tenth position of the decapeptide residue is the residue of valine.

43. The compound of claim 1, wherein M is an undecapeptide residue and the amino acid residue in the aminoterminal position of the undecapeptide residue is the residue of asparagine, glutamine, serine, aspartic acid, glutamic acid, lysine, alanine, threonine, methionine, arginine, histidine or leucine, the amino acid residue in the second position of the undecapeptide residue is the residue of alanine, valine, serine, leucine, lysine, threonine, glycine, glutamine, asparagine or histidine, the amino acid residue in the third position of the undecapeptide residue is the residue of isoleucine, leucine, valine, alanine, threonine, phenylalanine or methionine, the amino acid residue in the fourth position of the undecapeptide residue is the residue of phenylalanine, tyrosine, tryptophan, histidine, 1-naphthylalanine, 2-naphthylalanine, cyclohexylalanine or lysine, the amino acid residue in the fifth position of the undecapeptide residue is the residue of threonine, serine, lysine, methionine, leucine, isoleucine, alanine, asparagine, glutamine, aspartic acid, glutamic acid, cysteine or histidine, the amino acid residue in the sixth position of the undecapeptide residue is the residue of asparagine, aspartic acid, glutamine, glutamic acid, serine, lysine, alanine, threonine, cysteine or ornithine, the amino acid residue in the seventh position of the undecapeptide residue is the residue of serine, alanine, cysteine, threonine, lysine, valine, asparagine, aspartic acid, glutamine or glutamic acid, the amino acid residue in the eighth position of the undecapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the ninth position of the undecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the tenth position of the undecapeptide residue is the residue of lysine, arginine, ornithine, histidine, glutamine, alanine, glutamic acid, aspartic acid, asparagine, cysteine or serine, the amino acid residue in the eleventh position of the undecapeptide residue is the residue of valine, isoleucine, leucine, penicillamine, lysine, cysteine, glutamic acid, glutamic acid, aspartic acid, arginine, alanine, homocysteine, leucine, isoleucine, methionine, ornithine, phenylalanine or threonine.

44. The compound of claim 1, wherein M is an undecapeptide residue and the amino acid residue in the amino-terminal position of the undecapeptide residue is the residue of aspartic acid, the amino acid residue in the second position of the undecapeptide residue is the residue of alanine or asparagine, the amino acid residue in the third position of the undecapeptide residue is the residue of isoleucine, the amino acid residue in the fourth position of the undecapeptide residue is the residue of phenylalanine, the amino acid residue in the fifth position of the undecapeptide residue is the residue of threonine, the amino acid residue in the sixth position of the undecapeptide residue is the residue of aspartic acid, glutamine or ornithine, the amino acid residue in the seventh position of the undecapeptide residue is the residue of alanine, the amino acid residue in the eighth position of the undecapeptide residue is the residue of tyrosine, the amino acid residue in the ninth position of the undecapeptide residue is the residue of arginine, the amino acid residue in the tenth position of the undecapeptide residue is the residue of lysine, ornithine or aspartic acid, the amino acid residue in the eleventh position of the undecapeptide residue is the residue of valine.

45. The compound of claim 1 wherein M is a dodecapeptide residue and the amino acid residue in the aminoterminal position of the dodecapeptide residue is the residue of alanine or N-methylalanine, the amino acid residue in the second position of the dodecapeptide residue is the residue of aspartic acid, the amino acid residue in the third position of the dodecapeptide residue is the residue of alanine or asparagine, the amino acid residue in the fourth position of the dodecapeptide residue is the residue of isoleucine, the amino acid residue in the fifth position of the dodecapeptide residue is the residue of phenylalanine, the amino acid residue in the sixth position of the dodecapeptide residue is the residue of threonine, the amino acid residue in the seventh position of the dodecapeptide residue is the residue of aspartic acid, glutamine or ornithine, the amino acid residue in the eighth position of the dodecapeptide residue is the residue of alanine, the amino acid residue in the ninth position of the dodecapeptide residue is the residue of tyrosine, the amino acid residue in the tenth position of the dodecapeptide residue is the residue of arginine, the amino acid residue in the eleventh position of the dodecapeptide residue is the residue of lysine, ornithine or aspartic acid, the amino acid residue in the twelfth position of the dodecapeptide residue is the residue of valine.

46. The compound of claim 1 wherein M is a dodecapeptide residue and the amino acid residue in the aminoterminal position of the dodecapeptide residue is the residue of alanine, valine, leucine, serine, threonine, lysine, cysteine, glutamine, glutamic acid, asparagine, aspartic acid, glycine, N-methylalanine or histidine, the amino acid residue in the second position of the dodecapeptide residue is the residue of asparagine, glutamine, serine, aspartic acid, glutamic acid, lysine, alanine, threonine, methionine, arginine, histidine or leucine the amino acid residue in the third position of the dodecapeptide residue is the residue of alanine, valine, serine, leucine, lysine, threonine, glycine, glutamine, asparagine or histidine, the amino acid residue in the fourth position of the dodecapeptide residue is the residue of isoleucine, leucine, valine, alanine, threonine, phenylalanine or methionine, the amino acid residue in the fifth position of the dodecapeptide residue is the residue of phenylalanine, tyrosine, tryptophan, histidine, 1-naphthylalanine, 2-naphthylalanine, cyclohexylalanine or lysine, the amino acid residue in the sixth position of the dodecapeptide residue is the residue of threonine, serine, lysine, methionine, leucine, isoleucine, alanine, asparagine, glutamine, aspartic acid, glutamic acid, cysteine or histidine, the amino acid residue in the seventh position of the dodecapeptide residue is the residue of asparagine, aspartic acid, glutamine, glutamic acid, serine, lysine, alanine, threonine, cysteine or ornithine, the amino acid residue in the eighth position of the dodecapeptide residue is the residue of serine, alanine, cysteine, threonine, lysine, valine, asparagine, aspartic acid, glutamine or glutamic acid, the amino acid residue in the ninth position of the dodecapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the tenth position of the dodecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the eleventh position of the dodecapeptide residue is the residue of lysine, arginine, ornithine, histidine, glutamine, alanine, glutamic acid, aspartic acid, asparagine, cysteine or serine, the amino acid residue in the twelfth position of the dodecapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

47. The compound of claim 1, wherein M is a tredecapeptide residue and the amino acid residue in the aminoterminal position of the tredecapeptide residue is the residue of tyrosine, the amino acid residue in the second position of the tredecapeptide residue is the residue of alanine or N-methylalanine, the amino acid residue in the third position of the tredecapeptide residue is the residue of aspartic acid, the amino acid residue in the fourth position of the tredecapeptide residue is the residue of alanine or asparagine, the amino acid residue in the fifth position of the tredecapeptide residue is the residue of isoleucine, the amino acid residue in the sixth position of the tredecapeptide residue is the residue of phenylalanine, the amino acid residue in the seventh position of the tredecapeptide residue is the residue of threonine, the amino acid residue in the eighth position of the tredecapeptide residue is the residue of aspartic acid, glutamine or ornithine, the amino acid residue in the ninth position of the tredecapeptide residue is the residue alanine, the amino acid residue in the tenth position of the tredecapeptide residue is the residue of tyrosine, the amino acid residue in the eleventh position of the tredecapeptide residue is the residue of arginine, the amino acid residue in the twelfth position of the tredecapeptide residue is the residue lysine, ornithine or aspartic acid, the amino acid residue in the thirteenth position of the tredecapeptide residue is the residue of valine.

48. The compound of claim 1, wherein M is a tredecapeptide residue and the amino acid residue in the aminoterminal position of the tredecapeptide residue is the residue of tyrosine, histidine, phenylalanine, tryptophan, lysine, 1-naphthylalanine, 2-naphthylalanine, biphenylalanine, glutamine or asparagine, the amino acid residue in the second position of the tredecapeptide residue is the residue of alanine, valine, leucine, serine, threonine, lysine, cysteine, glutamine, glutamic acid, asparagine, aspartic acid, glycine, N-methylalanine or histidine, the amino acid residue in the third position of the tredecapeptide residue is the residue of asparagine, glutamine, serine, aspartic acid, glutamic acid, lysine, alanine, threonine, methionine, arginine, histidine or leucine, the amino acid residue in the fourth position of the tredecapeptide residue is the residue of alanine, valine, serine, leucine, lysine, threonine, glycine, glutamine, asparagine or histidine, the amino acid residue in the fifth position of the tredecapeptide residue is the residue of isoleucine, leucine, valine, alanine, threonine, phenylalanine or methionine, the amino acid residue in the sixth position of the tredecapeptide residue is the residue of phenylalanine, tyrosine, tryptophan, histidine, 1-naphthylalanine, 2-naphthylalanine, cyclohexylalanine or lysine, the amino acid residue in the seventh position of the tredecapeptide residue is the residue of threonine, serine, lysine, methionine, leucine, isoleucine, alanine, asparagine, glutamine, aspartic acid, glutamic acid, cysteine or histidine, the amino acid residue in the eighth position of the tredecapeptide residue is the residue of asparagine, aspartic acid, glutamine, glutamic acid, serine, lysine, alanine, threonine, cysteine or ornithine, the amino acid residue in the ninth position of the tredecapeptide residue is the residue of serine, alanine, cysteine, threonine, lysine, valine, asparagine, aspartic acid, glutamine or glutamic acid, the amino acid residue in the tenth position of the tredecapeptide residue is the residue of tyrosine, phenylalanine, histidine, glutamine, lysine, tryptophan, 1-naphthylalanine, 2-naphthylalanine, biphenylalanine, alanine, glutamic acid or cysteine, the amino acid residue in the eleventh position of the tredecapeptide residue is the residue of lysine, arginine, ornithine, histidine, glutamine, alanine, serine, glutamic acid, aspartic acid, cysteine, 4-aminophenylalanine, 4-guanidinophenylalanine or asparagine, the amino acid residue in the twelfth position of the tredecapeptide residue is the residue of lysine, arginine, ornithine, histidine, glutamine, alanine, glutamic acid, aspartic acid, asparagine, cysteine or serine, the amino acid residue in the thirteenth position of the tredecapeptide residue is the residue of valine, isoleucine, leucine, penicillamine, lysine, cysteine, glutamic acid, glutamine, aspartic acid, arginine, alanine, homocysteine, leucine, isoleucine, methionine, ornithine, phenylalanine or threonine.

49. The compound of claim 1, wherein N is the residue of lysine, histidine, ornithine, arginine, glutamine, glutamic acid, aspartic acid, asparagine, serine, alanine, cysteine, tyrosine, tryptophan, phenylalanine, or homocysteine.

50. The compound of claim 1, wherein N is the residue of lysine or histidine.

51. The compound of claim 1, wherein N is a dipeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the carboxyterminal position is the residue of leucine, alanine, cyclohexylalanine, glutamic acid, lysine, aspartic acid, cysteine, valine, isoleucine, methionine, histidine, threonine or phenylalanine.

52. The compound of claim 1, wherein N is a dipeptide residue and the amino acid residue in the first position is the residue of lysine or histidine, the amino acid residue in the carboxyterminal position is the residue of leucine.

53. The compound of claim 1, wherein N is a tripeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the carboxyterminal position is the residue of leucine, alanine, cyclohexylalanine, glutamic acid, lysine, aspartic acid, cysteine, valine, isoleucine, methionine, histidine, threonine or phenylalanine.

54. The compound of claim 1, wherein N is a tripeptide residue and the amino acid residue in the first position is the residue of lysine or histidine, the amino acid residue in the second position is the residue of leucine, the amino acid residue in the carboxyterminal position is the residue leucine.

55. The compound of claim 1, wherein N is a tetrapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the carboxyterminal position is the residue of glutamine, glutamic acid, aspartic acid, asparagine, lysine, serine, arginine, ornithine, histidine, cysteine, methionine, threonine, tyrosine, alanine or leucine.

56. The compound of claim 1, wherein N is a tetrapeptide residue and the amino acid residue in the first position is the residue of lysine or histidine, the amino acid residue in the second position is the residue of leucine, the amino acid residue in the third position is the residue of leucine, the amino acid residue in the carboxyterminal position is the residue of glutamine.

57. The compound of claim 1, wherein N is a pentapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, the amino acid residue in the carboxyterminal position is the residue of asparagine, histidine, glutamine, aspartic acid, glutamic acid, lysine, ornithine, serine, methionine, threonine or alanine.

58. The compound of claim 1, wherein N is a pentapeptide residue and the amino acid residue in the first position is the residue of lysine or histidine, the amino acid residue in the second position is the residue of leucine, the amino acid residue in the third position is the residue leucine, the amino acid residue in the fourth position is the residue of glutamine, the amino acid residue in the carboxyterminal position is the residue of histidine.

59. The compound of claim 1, wherein N is a hexapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, the amino acid residue in the fifth position is the residue of asparagine, histidine, glutamine, aspartic acid, glutamic acid, lysine, ornithine, serine, methionine, threonine or alanine, the amino acid residue in the carboxyterminal position is the residue of isoleucine, valine, threonine, glutamic acid, aspartic acid, lysine, cysteine, penicillamine, homocysteine, methionine, histidine, leucine or alanine.

60. The compound of claim 1, wherein N is a hexapeptide residue and the amino acid residue in the first position is the residue of lysine or histidine, the amino acid residue in the second position is the residue of leucine, the amino acid residue in the third position is the residue of leucine, the amino acid residue in the fourth position is the residue of glutamine, the amino acid residue in the fifth position is the residue of histidine, the amino acid residue in the carboxyterminal position is the residue of isoleucine, valine, threonine, glutamic acid, aspartic acid, lysine, cysteine, penicillamine, homocysteine, methionine, histidine, leucine or alanine.

61. The compound of claim 1, wherein N is a heptapeptide residue and the amino acid residue in the first position is the residue of histidine or lysine, the amino acid residue in the second position is the residue of leucine, the amino acid residue in the third position is the residue of leucine, the amino acid residue in the fourth position is the residue of glutamine, the amino acid residue in the fifth position is the residue of histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the carboxyterminal position is the residue of methionine, norleucine, homocysteine, leucine, glutamine, glutamic acid, aspartic acid, lysine, ornithine, histidine, threonine, asparagine, alanine or serine.

62. The compound of claim 1, wherein N is a heptapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, the amino acid residue in the fifth position is the residue of asparagine, histidine, glutamine, aspartic acid, glutamic acid, lysine, ornithine, serine, methionine, threonine or alanine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the carboxyterminal position is the residue of methionine, norleucine, homocysteine, leucine, glutamine., glutamic acid, aspartic acid, lysine, ornithine, histidine, threonine, asparagine, alanine or serine.

63. The compound of claim 1, wherein N is an octapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, preferably glutamine, the amino acid residue in the fifth position is the residue of asparagine, histidine, glutamine, aspartic acid, glutamic acid, lysine, ornithine, serine, methionine, threonine or alanine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the carboxyterminal position is the residue of serine, threonine, alanine, cysteine, asparagine, aspartic acid, glutamic acid, glutamine, histidine, arginine, tyrosine or homocysteine.

64. The compound of claim 1, wherein N is an octapeptide residue and the amino acid residue in the first position is the residue of histidine or lysine, the amino acid residue in the second position is the residue of leucine, the amino acid residue in the third position is the residue of leucine, the amino acid residue in the fourth position is the residue of glutamine, the amino acid residue in the fifth position is the residue of histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the carboxyterminal position is the residue of serine, threonine, alanine, cysteine, asparagine, aspartic acid, glutamic acid, glutamine, histidine, arginine, tyrosine or homocysteine.

65. The compound of claim 1, wherein N is a nonapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, alanine, cyclohexylalanine, glutamic acid, lysine, aspartic acid, cysteine, valine, isoleucine, methionine, histidine, threonine or phenylalanine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, the amino acid residue in the fifth position is the residue of asparagine, histidine, glutamine, aspartic acid, glutamic acid, lysine, ornithine, serine, methionine, threonine or alanine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the carboxyterminal position is the residue of arginine, lysine, ornithine, histidine, glutamine, glutamic acid, asparagine, aspartic acid, serine, tyrosine, homocysteine or alanine.

66. The compound of claim 1, wherein N is a nonapeptide residue and the amino acid residue in the first position is the residue of histidine or lysine, the amino acid residue in the second position is the residue of leucine, the amino acid residue in the third position is the residue of leucine, the amino acid residue in the fourth position is the residue of glutamine, the amino acid residue in the fifth position is the residue of histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the carboxyterminal position is the residue of arginine, lysine, ornithine, histidine, glutamine, glutamic acid, asparagine, aspartic acid, serine, tyrosine, homocysteine or alanine.

67. The compound of claim 1, wherein N is a decapeptide residue and the amino acid residue in the first position is the residue of lysine, histidine, ornithine, arginine, glutamine, glutamic acid, aspartic acid, asparagine, serine, alanine, cysteine, tyrosine, tryptophan, phenylalanine or homocysteine, the amino acid residue in the second position is the residue of leucine, the amino acid residue in the third position is the residue of leucine, alanine, cyclohexylalanine, glutamic acid, lysine, aspartic acid, cysteine, valine, isoleucine, methionine, histidine, threonine or phenylalanine, the amino acid residue in the fourth position is the residue of glutamine, glutamic acid, aspartic acid, asparagine, lysine, serine, arginine, ornithine, histidine, cysteine, methionine, threonine, tyrosine, alanine or leucine, the amino acid residue in the fifth position is the residue of asparagine, histidine, glutamine, aspartic acid, glutamic acid, lysine, ornithine, serine, methionine, threonine or alanine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the ninth position is the residue of arginine, lysine, ornithine, histidine, glutamine, glutamic acid, asparagine, aspartic acid, serine, tyrosine, homocysteine or alanine, the amino acid residue in the carboxyterminal position is the residue of glutamine, glutamic acid, histidine, lysine, asparagine, aspartic acid, arginine, serine, threonine or tyrosine.

68. The compound of claim 1, wherein N is a decapeptide residue and the amino acid residue in the first position is the residue of lysine or histidine, the amino acid residue in the second position is the residue of leucine, the amino acid residue in the third position is the residue of leucine, the amino acid residue in the fourth position is the residue of glutamine, the amino acid residue in the fifth position is the residue of histidine, the amino acid residue in the sixth position is the residue of isoleucine, valine, threonine, glutamic acid, aspartic acid, lysine, cysteine, penicillamine, homocysteine, methionine, histidine, leucine or alanine, the amino acid residue in the seventh position is the residue of methionine, norleucine, homocysteine, leucine, glutamine, glutamic acid, aspartic acid, lysine, ornithine, histidine, threonine, asparagine, alanine or serine, the amino acid residue in the eighth position is the residue of serine, threonine, alanine, cysteine, asparagine, aspartic acid, glutamic acid, glutamine, histidine, arginine, tyrosine or homocysteine, the amino acid residue in the ninth position is the residue of arginine, lysine, ornithine, histidine, glutamine, glutamic acid, asparagine, aspartic acid, serine, tyrosine, homocysteine or alanine, the amino acid residue in the carboxyterminal position is the residue of glutamine, glutamic acid, histidine, lysine, asparagine, aspartic acid, arginine, serine, threonine or tyrosine.

69. The compound of claim 1, wherein K is hydrogen or a group of formula $W^1—(CH_2)_{v^1}—CO—$, wherein $W^1$ is hydrogen, hydroxy or $C_{1-6}$-alkyl, and $v^1$ is 0, 1, 2, 3 or 4.

70. The compound of claim 1, wherein K is hydrogen or a group of formula $W^1—(CH_2)_{v^1}—CO—$, wherein $W^1$ is hydrogen, and $v^1$ is 1.

71. The compound of claim 1, wherein L is

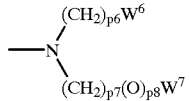

wherein p6 and p7 independently are 0; $W^6$ is hydrogen, p8 is 0; $W^7$ is hydrogen.

72. The compound of claim 1, wherein L is

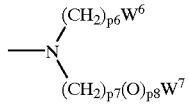

wherein p6 and p7 independently are 0,1, or 2; $W^6$ is hydrogen, hydroxy, or $C_{1-6}$-alkyl, p8 is 0 or 1; $W^7$ is hydrogen, hydroxy, or $C_{1-6}$ alkyl.

73. A compound of claim 1 selected from the group consisting of:

Asp-Ala-Tyr-Arg-Lys-Val-Leu-Ala-Gln-Leu-Ser-Ala-Arg-His-NH$_2$ (SEQ ID NO:1),
Ac-Asp-Ala-Tyr-Arg-Lys-Val-Leu-Ala-Gln-Leu-Ser-Ala-Arg-His-NH$_2$ (SEQ ID NO:2),
Asp-Ala-Tyr-Arg-Ala-Val-Leu-Ala-Gln-Leu-Ser-Ala-Arg-His-NH$_2$ (SEQ ID NO:3),
Asp-Tyr-Arg-Lys-Val-Leu-Ala-Gln-Leu-Ser-Ala-Arg-His-NH$_2$ (SEQ ID NO:4),
Asp-Ala-Tyr-Arg-Lys-Val-Leu-Ala-Gln-Leu-homoArg-His-NH$_2$ (SEQ ID NO:5),
Asp-Ala-Tyr-Arg-Ala-Val-Leu-Ala-Gln-Leu-homoArg-His-NH$_2$ (SEQ ID NO:6),
Asp-Tyr-Arg-Ala-Val-Leu-Ala-Gln-Leu-homoArg-His-NH$_2$ (SEQ ID NO:7),
Asp-Arg-Lys-Val-Leu-Ala-Gln-Leu-Ser-Ala-Arg-His-NH$_2$ (SEQ ID NO:8),
Asp-Lys-Val-Leu-Ala-Gln-Leu-Ser-Ala-Arg-His-NH$_2$ (SEQ ID NO:9),
Asp-Val-Leu-Ala-Gln-Leu-Ser-Ala-Arg-His-NH$_2$ (SEQ ID NO:10),
Asp-Leu-Ala-Gln-Leu-Ser-Ala-Arg-His-NH$_2$ (SEQ ID NO:11),
Ac-Asp-Ala-Tyr-Arg-Lys-Val-Leu-Ala-Glu-Leu-Ser-Ala-Arg-His-NH$_2$ (SEQ ID NO:12),
Asp-Ala-Tyr-Arg-Lys-Val-Leu-Ala-Glu-Leu-Ser-Ala-Arg-His-NH$_2$ (SEQ ID NO:13),
Cyclo(Glu$^9$-Lys$^{13}$)-Asp-Ala-Tyr-Arg-Lys-Val-Leu-Ala-Glu-Leu-Ser-Ala-Lys-His-NH$_2$ (SEQ ID NO:14),
Cyclo(Lys$^5$-Glu$^9$)-Asp-Ala-Tyr-Arg-Lys-Val-Leu-Ala-Glu-Leu-Ser-Ala-Arg-His-NH$_2$ (SEQ ID NO:15),
Asp-Tyr-Arg-Lys-Val-Leu-Glu-Gln-Leu-Arg-His-NH$_2$ (SEQ ID NO:16),
Asp-Ala-Tyr-Arg-Lys-Val-Phe-Ala-Gln-Leu-Ser-Ala-Arg-His-NH$_2$ (SEQ ID NO:17),
Asp-Ala-Tyr-Arg-Lys-Val-Leu-Ala-Gln-Phe-Ser-Ala-Arg-His-NH$_2$ (SEQ ID NO:18),
Asp-Ala-Tyr-Arg-Lys-Val-Leu-Ala-Gln-Leu-Tyr-Ala-Arg-His-NH$_2$ (SEQ ID NO:19),
Asp-Ala-Gln-Arg-Lys-Val-Leu-Ala-Gln-Leu-Ser-Ala-Arg-His-NH$_2$ (SEQ ID NO:20),
Glu-Val-Leu-Arg-Glu-Leu-Ser-Ala-Arg-His-NH$_2$ (SEQ ID NO:21),
Cyclo(Asp$^1$-[Gly]-Orn$^5$)-Asp-Ala-Tyr-Arg-Orn-Val-Leu-Ala-Gln-Leu-Ser-Ala-Arg-His-NH$_2$ (SEQ ID NO:22),
Lys-Val-Leu-Ala-Gln-Leu-Ser-Ala-Arg-Lys-Leu-Leu-Gln-His-NH$_2$ (SEQ ID NO:23),
Asp-Ala-Tyr-Arg-Lys-Val-Leu-Ala-Gln-Leu-Ser-Ala-Lys-His-NH$_2$ (SEQ ID NO:24),
Ac-Asp-Ala-Tyr-Arg-Lys-Val-Leu-Ala-Gln-Leu-Ser-Ala-Lys-His-NH$_2$ (SEQ ID NO:25),
Cyclo(Lys$^2$-Glu$^6$)-Arg-Lys-Val-Leu-Ala-Glu-Leu-Ser-Ala-Arg-His-NH$^2$(SEQ ID NO:26),
Cyclo(Lys$^4$-Glu$^8$)-Lys-Val-Leu-Lys-Gln-Leu-Ser-Glu-Arg-NH$_2$ (SEQ ID NO:27),
Cyclo(Orn$^2$-[COCH$_2$]-Pen$^6$)-(Asp-Orn-Tyr-Arg-Lys-Pen-Leu-Ala-Gln-Leu-Ser-Ala-Arg-His-NH$_2$ (SEQ ID NO:28),
Lys-Val-Leu-Ala-Gln-Leu-Ser-Ala-Arg-NH$_2$ (SEQ ID NO:29),
Cyclo(Lys$^3$-Glu$^7$)-Lys-Val-Leu-Lys-Gln-Leu-Ser-Glu-Arg-His-NH$_2$(SEQ ID NO:30),
Cyclo(Lys$^2$-Glu$^6$)-Arg-Lys-Val-Leu-Ala-Glu-Leu-Ser-Ala-Arg-His-NH$_2$(SEQ ID NO:31),
Cyclo(Lys$^3$-Glu$^7$)-Tyr-Arg-Lys-Val-Leu-Ala-Glu-Leu-Ser-Ala-Arg-His-NH$_2$ (SEQ ID NO:32),
Cyclo(Glu$^1$-Lys$^5$)-Glu-Ala-Tyr-Arg-Lys-Val-Leu-Ala-Glu-Leu-Ser-Ala-Arg-His-NH$_2$ (SEQ ID NO:33),
Cyclo(Lys$^4$-Glu$^8$)-Asp-Ala-Tyr-Lys-Lys-Val-Leu-Glu-Gln-Leu-Ser-Ala-Arg-His-NH$_2$ (SEQ ID NO:34),
Cyclo(Lys$^3$-Glu$^7$)-Ala-Tyr-Lys-Lys-Val-Leu-Glu-Gln-Leu-Ser-Ala-Arg-His-NH$_2$ (SEQ ID NO:35),
Cyclo(Lys$^4$-Glu$^8$)-Ala-Tyr-Arg-Lys-Val-Leu-Ala-Glu-Leu-Ser-Ala-Arg-His-NH$_2$ (SEQ ID NO:36),
and
Arg-Lys-Val-Leu-Ala-Gln-Leu-Ser-Ala-Arg-NH$_2$ (SEQ ID NO:37);
or a pharmaceutically acceptable salt thereof.

74. A pharmaceutical composition comprising, as an active ingredient, a compound of claim 1 together with a pharmaceutically acceptable carrier or diluent.

75. The composition of claim 74 in unit dosage form, comprising from about 10 to about 200 mg of the compound.

76. A compound of claim 1 selected from the group consisting of:

H-Tyr-Ala-Asp-Ala-Ile-Phe-Thr-Asp-Ala-Tyr-Arg-Lys-Val-Leu-Ala-Gln-Leu-Ser-Ala-Arg-His-NH$_2$ (SEQ ID NO:38),
Ac-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:39),
Ac-Ala-Asp-Ala-Ile-Phe-Thr-Asp-Ala-Tyr-Arg-Lys-Val-Leu-Ala-Gln-Leu-Ser-Ala-Arg-Lys-Leu-Leu-Gln-His-NH$_2$ (SEQ ID NO:40),

Cyclo(Asp²-[Gly]-Orn⁶)-Ac-Asp-Asp-Ile-Phe-Thr-Orn-Ala-Tyr-Arg-Lys-Val-Leu-Ala -Gln-Leu-Ser-Ala-Arg-Lys-Leu-Leu-Gln-His-NH₂ (SEQ ID NO:41), Cyclo(Asp⁶-[Gly]-Orn¹⁰)-Ac-Asp-Ala-Ile-Phe-Thr-Asp-Ala-Tyr-Arg-Orn-Val-Leu-Ala -Gln-Leu-Ser-Ala-Arg-Lys-Leu-Leu-Gln-His-NH₂ (SEQ ID NO:42), Cyclo(Asp¹⁰-[Gly]-Orn¹⁴)-Ac-Asp-Ala-Ile-Phe-Thr-Asp-Ala-Tyr-Arg-Asp-Val-Leu -Ala-Orn-Leu-Ser-Ala-Arg-Lys-Leu-Leu-Gln-His-NH₂ (SEQ ID NO:43), and Ac-(N-Me)Ala-Asp-Ala-Ile-Phe-Thr-Asp-Ala-Tyr-Arg-Lys-Val-Leu-Ala-Gln-Leu-Ser -Ala-Arg-Lys-Leu-Leu-Gln-His-NH₂ (SEQ ID NO:44);

or a pharmaceutically acceptable salt thereof.

77. A method of stimulating the release of growth hormone from the pituitary, the method comprising administering to a subject in need thereof an effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 5,990,084

DATED : November 23, 1999

INVENTOR(S) : Richter et al.

It is certified that error appears in the above-identified patent and that said Letters Patent is hereby corrected as shown below:

IN THE CLAIMS:

Column 49, line 24, please delete "Z", and insert --z--.

Column 53, line 47, please delete "o r", and insert --or--.

Column 55, line 61, please delete "5", and insert --8--

Column 55, line 64, please delete "5", and insert --8--

Signed and Sealed this

Fifteenth Day of May, 2001

Attest:

NICHOLAS P. GODICI

*Attesting Officer*  *Acting Director of the United States Patent and Trademark Office*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:1:

Asp Ala Tyr Arg Lys Val Leu Ala Gln Leu Ser Ala Arg His
1               5                  10

(2) INFORMATION FOR SEQ ID NO:2:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:2:

Asp Ala Tyr Arg Lys Val Leu Ala Gln Leu Ser Ala Arg His
1               5                  10

(2) INFORMATION FOR SEQ ID NO:3:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:3:

Asp Ala Tyr Arg Ala Val Leu Ala Gln Leu Ser Ala Arg His
1               5                  10

(2) INFORMATION FOR SEQ ID NO:4:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:4:

Asp Tyr Arg Lys Val Leu Ala Gln Leu Ser Ala Arg His
1               5                  10

(2) INFORMATION FOR SEQ ID NO:5:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:5:

Asp Ala Tyr Arg Lys Val Leu Ala Gln Leu Arg His
1               5                  10

(2) INFORMATION FOR SEQ ID NO:6:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:6:

Asp Ala Tyr Arg Ala Val Leu Ala Gln Leu Arg His
1               5                   10

(2) INFORMATION FOR SEQ ID NO:7:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:7:

Asp Tyr Arg Ala Val Leu Ala Gln Leu Arg His
1               5                   10

(2) INFORMATION FOR SEQ ID NO:8:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:8:

Asp Arg Lys Val Leu Ala Gln Leu Ser Ala Arg His
1               5                   10

(2) INFORMATION FOR SEQ ID NO:9:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:9:

Asp Lys Val Leu Ala Gln Leu Ser Ala Arg His
1               5                   10

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:10:

Asp Val Leu Ala Gln Leu Ser Ala Arg His
1               5                   10

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:11:

Asp Leu Ala Gln Leu Ser Ala Arg His
1               5

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:12:

Asp Ala Tyr Arg Lys Val Leu Ala Glu Leu Ser Ala Arg His
1               5                  10

(2) INFORMATION FOR SEQ ID NO:13:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:13:

Asp Ala Tyr Arg Lys Val Leu Ala Glu Leu Ser Ala Arg His
1               5                  10

(2) INFORMATION FOR SEQ ID NO:14:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:14:

Asp Ala Tyr Arg Lys Val Leu Ala Glu Leu Ser Ala Lys His
1               5                  10

(2) INFORMATION FOR SEQ ID NO:15:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:15:

Asp Ala Tyr Arg Lys Val Leu Ala Glu Leu Ser Ala Arg His
1               5                  10

(2) INFORMATION FOR SEQ ID NO:16:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: None -continued (xi) SEQUENCE DESCRIPTION: SEQ ID NO:16:

Asp Tyr Arg Lys Val Leu Glu Gln Leu Arg His
1               5                   10

(2) INFORMATION FOR SEQ ID NO:17:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:17:

Asp Ala Tyr Arg Lys Val Phe Ala Gln Leu Ser Ala Arg His
1               5                   10

(2) INFORMATION FOR SEQ ID NO:18:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:18:

Asp Ala Tyr Arg Lys Val Leu Ala Gln Phe Ser Ala Arg His
1               5                   10

(2) INFORMATION FOR SEQ ID NO:19:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:19:

Asp Ala Tyr Arg Lys Val Leu Ala Gln Leu Tyr Ala Arg His
1               5                   10

(2) INFORMATION FOR SEQ ID NO:20:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:20:

Asp Ala Gln Arg Lys Val Leu Ala Gln Leu Ser Ala Arg His
1               5                   10

(2) INFORMATION FOR SEQ ID NO:21:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:21:

Glu Val Leu Arg Glu Leu Ser Ala Arg His
1               5                   10

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

Asp Ala Tyr Arg Val Leu Ala Gln Leu Ser Ala Arg His
1               5                   10

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Lys Val Leu Ala Gln Leu Ser Ala Arg Lys Leu Leu Gln His
1               5                   10

(2) INFORMATION FOR SEQ ID NO:24:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Asp Ala Tyr Arg Lys Val Leu Ala Gln Leu Ser Ala Lys His
1               5                   10

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

Asp Ala Tyr Arg Lys Val Leu Ala Gln Leu Ser Ala Lys
1               5                   10

(2) INFORMATION FOR SEQ ID NO:26:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Arg Lys Val Leu Ala Glu Leu Ser Ala Arg His
1               5                   10

(2) INFORMATION FOR SEQ ID NO:27:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:27:

Lys Val Leu Lys Gln Leu Ser Glu Arg
1               5

(2) INFORMATION FOR SEQ ID NO:28:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:28:

Asp Tyr Arg Lys Xaa Leu Ala Gln Leu Ser Ala Arg His
1               5                   10

(2) INFORMATION FOR SEQ ID NO:29:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:29:

Lys Val Leu Ala Gln Leu Ser Ala Arg
1               5

(2) INFORMATION FOR SEQ ID NO:30:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:30:

Lys Val Leu Lys Gln Leu Ser Glu Arg His
1               5                   10

(2) INFORMATION FOR SEQ ID NO:31:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: None (xi) SEQUENCE DESCRIPTION: SEQ ID NO:31:

Arg Lys Val Leu Ala Glu Leu Ser Ala Arg His
1               5                   10

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

Tyr Arg Lys Val Leu Ala Glu Leu Ser Ala Arg His
1               5                   10

(2) INFORMATION FOR SEQ ID NO:33:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Glu Ala Tyr Arg Lys Val Leu Ala Glu Leu Ser Ala Arg His
1               5                   10

(2) INFORMATION FOR SEQ ID NO:34:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

Asp Ala Tyr Lys Lys Val Leu Glu Gln Leu Ser Ala Arg His
1               5                   10

(2) INFORMATION FOR SEQ ID NO:35:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

Ala Tyr Lys Lys Val Leu Glu Gln Leu Ser Ala Arg His
1               5                   10

(2) INFORMATION FOR SEQ ID NO:36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

Ala Tyr Arg Lys Val Leu Ala Glu Leu Ser Ala Arg His
1               5                  10

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:37:

Arg Lys Val Leu Ala Gln Leu Ser Ala Arg
1               5                  10

(2) INFORMATION FOR SEQ ID NO:38:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:38:

Tyr Ala Asp Ala Ile Phe Thr Asp Ala Tyr Arg Lys Val Leu Ala Gln
1               5                  10                  15

Leu Ser Ala Arg His
            20

(2) INFORMATION FOR SEQ ID NO:39:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:39:

Asp Ala Ile Phe Thr Asp Ala Tyr Arg Lys Val Leu Ala Gln Leu Ser
1               5                  10                  15

Ala Arg Lys Leu Leu Gln His
            20

(2) INFORMATION FOR SEQ ID NO:40:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:40:

Ala Asp Ala Ile Phe Thr Asp Ala Tyr Arg Lys Val Leu Ala Gln Leu
1               5                  10                  15

Ser Ala Arg Lys Leu Leu Gln His
            20

(2) INFORMATION FOR SEQ ID NO:41:

```
    (i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

Asp Asp Ile Phe Thr Ala Tyr Arg Lys Val Leu Ala Gln Leu Ser Ala
1               5                   10                  15

Arg Lys Leu Leu Gln His
            20

(2) INFORMATION FOR SEQ ID NO:42:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

Asp Ala Ile Phe Thr Asp Ala Tyr Arg Val Leu Ala Gln Leu Ser Ala
1               5                   10                  15

Arg Lys Leu Leu Gln His
            20

(2) INFORMATION FOR SEQ ID NO:43:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

Asp Ala Ile Phe Thr Asp Ala Tyr Arg Asp Val Leu Ala Leu Ser Ala
1               5                   10                  15

Arg Lys Leu Leu Gln His
            20

(2) INFORMATION FOR SEQ ID NO:44:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

Ala Asp Ala Ile Phe Thr Asp Ala Tyr Arg Lys Val Leu Ala Gln Leu
1               5                   10                  15

Ser Ala Arg Lys Leu Leu Gln His
            20

(2) INFORMATION FOR SEQ ID NO:45:

(i) SEQUENCE CHARACTERISTICS:
        (A) LENGTH: 21 amino acids
        (B) TYPE: amino acid
```

```
        (C) STRANDEDNESS: single
        (D) TOPOLOGY: linear (ii) MOLECULE TYPE: None (xi) SEQUENCE DESCRIPTION: SEQ ID NO:45:

Tyr Ala Asp Ala Ile Phe Thr Gln Ser Tyr Arg Lys Val Leu Ala Gln
1               5                   10                  15

Leu Ser Ala Arg His
            20
```